United States Patent [19]

Larkin et al.

[11] Patent Number: 5,204,333
[45] Date of Patent: Apr. 20, 1993

[54] PESTICIDAL COMPOUNDS

[76] Inventors: John P. Larkin; John B. Weston; Ian H. Smith, all of The Wellcome Foundation Limited, Berkhamsted, Hertfordshire; Christopher J. Palmer, 37, Clapgate Lane, Ipswich, Suffolk, all of England; John E. Casida, 1570 La Vereda Rd., Berkeley, Calif. 94708

[21] Appl. No.: 839,685

[22] Filed: Feb. 24, 1992

Related U.S. Application Data

[63] Continuation of Ser. No. 469,013, Jan. 23, 1990, abandoned.

[30] Foreign Application Priority Data

Jan. 24, 1989 [GB] United Kingdom ............... 8901490
Jan. 24, 1989 [GB] United Kingdom ............... 8901491

[51] Int. Cl.$^5$ .................. C07D 493/08; A01N 43/90
[52] U.S. Cl. ........................ 514/63; 514/456; 549/214; 549/215; 549/363
[58] Field of Search ................. 549/214, 215, 363; 514/63, 456

[56] References Cited

U.S. PATENT DOCUMENTS 2,097,114  6/1935  Butz .................... 549/363 X
3,328,427  6/1967  Melaas .................. 549/363

FOREIGN PATENT DOCUMENTS 152229  8/1985  European Pat. Off. .
211598  2/1987  European Pat. Off. .
216624  4/1987  European Pat. Off. .
216625  4/1987  European Pat. Off. .

OTHER PUBLICATIONS

Franzen, et al. "The Origin of the Anisochronism of Geminal Groups . . . ", J. Am. Chem. Soc. vol. 95 pp. 175-182 (1973).
D. J. Martin, et al. "A Simple Thiol Synthesis" J. Org. Chem. vol. 33 No. 3 Mar. 1968 pp. 1275-1276.
McElvain, et al. "Ketene Acetals XXXIV" J. Am. Chem. Soc. vol. 77 pp. 4571-4577, Sep. 5, 1955.

*Primary Examiner*—Marianne M. Cintins
*Assistant Examiner*—Catherine S. Kilby Scalzo
*Attorney, Agent, or Firm*—Nixon & Vanderhye

[57] ABSTRACT

The present invention provides compounds of the formula (I):

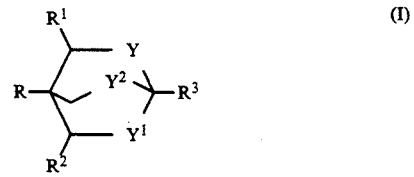

wherein R is a phenyl group, substituted fluorine atoms formulations containing them and their use in controlling pest infestation.

12 Claims, No Drawings

PESTICIDAL COMPOUNDS

This is a continuation of application Ser. No. 07/469,013, filed Jan. 23, 1990, now abandoned.

The present invention relates to novel chemical compounds having pesticidal activity, to methods for their preparation, to compositions containing them and to their use in the control of pests. More particularly the invention relates to a class of heterobicycloalkanes.

The use of certain 2,6,7-trioxabicyclo[2.2.2]octanes is disclosed in European Patent Application Nos. 152229, 211598, 216625 and 216624. It has now been discovered that certain of these compounds have particularly interesting pesticidal activity.

Accordingly, the present invention provides a compound of the formula (I):

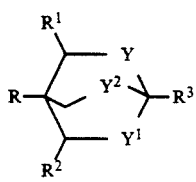

wherein R is a phenyl group, substituted by 1 to 5 fluorine atoms and optionally substituted at the para position by methyl or chloro or R is a group

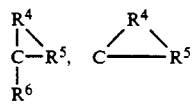

being a three or four membered ring, where $R^4$ is oxygen or a group $CR^7R^8$ wherein groups $R^7$, $R^8$ are the same or different and each is hydrogen, fluoro, chloro or bromo or methyl or ethyl optionally substituted by 1 to 3 fluoro atoms, and when

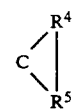

is a three-membered ring $R^5$ is a group $CR^{7a}R^{8a}$ wherein $R^{7a}$, $R^{8a}$ are the same or different and each is hydrogen, fluoro, chloro or bromo or methyl or ethyl optionally substituted by 1 to 3 fluoro atoms, or when

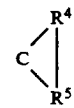

is a four membered ring $R^5$ is a group $CR^{7a}R^{8a}CR^9R^{10}$ wherein $R^{7a}$, $R^{8a}$ are as hereinbefore defined and $R^9$ and $R^{10}$ are the same or different and each is hydrogen, fluoro, chloro or bromo or methyl or ethyl optionally substituted by 1 to 3 fluoro atoms; $R^6$ is hydrogen, fluoro, chloro or methyl;

$R^1$ and $R^2$ may be the same or different, and each is hydrogen, halo, or a $C_{1-3}$ aliphatic group optionally substituted by halo, cyano, $C_{2-5}$ carbalkoxy, $C_{1-4}$ alkoxy, or a group $S(O)_m R^{11}$ wherein m is 0, 1 or 2 and $R^{11}$ is $C_{1-4}$ alkyl; cyano, gem dimethyl, or $C_{2-5}$ carbalkoxy; $R^3$ contains between 3 and 18 carbon atoms and is a group $R^{12}$ wherein $R^{12}$ is a $C_{1-13}$ non-aromatic hydrocarbyl group, optionally substituted by a $C_{2-4}$ carbalkoxy or cyano group and/or by one or two hydroxy groups and/or by one to five halo atoms which are the same or different and/or by one to three groups $R^{13}$ which are the same or different and each contains one to four hetero atoms, which are the same or different and are chosen from oxygen, sulphur, nitrogen and silicon, 1 to 10 carbon atoms and optionally 1 to 6 fluoro or chloro atoms or $R^3$ is a 6-membered aromatic ring substituted by cyano and/or by one to five halo atoms and/or by one to three $C_{2-4}$ haloalkyl groups and/or by a group —C≡CH, —C≡C-halo, —C≡C—$R^{12}$ wherein $R^{12}$ is as hereinbefore defined or —C≡C—$R^{14}$ wherein $R^{14}$ is a group $S(O)_q R^{15}$ wherein q is 0, 1 or 2 and $R^{15}$ is methyl, ethyl or trifluoromethyl or $R^{14}$ is $SiR^{16}R^{17}R^{18}$ wherein $R^{16}$ and $R^{17}$ are the same or different and are each $C_{1-4}$ aliphatic groups and $R^{18}$ is a $C_{1-4}$ aliphatic group or phenyl provided that $R^{16}$, $R^{17}$ and $R^{18}$ do not contain more than 10 carbon atoms in total; and Y, $Y^1$ and $Y^2$ are the same or different and are each selected from oxygen and $S(O)_t$ where t is 0, 1 or 2.

By the term "halo" is meant fluoro, chloro, bromo or iodo.

By the term "non-aromatic hydrocarbyl" group is meant an alkyl, alkenyl or alkynyl group (including a cyclic alkyl or alkenyl group optionally substituted by alkyl, alkenyl or alkynyl; and alkyl or alkenyl substituted by cyclic alkyl and alkenyl).

By the term "6-membered aromatic ring" is meant phenyl and heteroaromatic rings such as pyridyl.

In one embodiment of the present invention R is a phenyl group substituted by 1 to 5 fluorine atoms and optionally substituted at the para position by methyl or chloro.

Suitably R is phenyl substituted by one or two fluorine atoms.

In a second embodiment of the present invention R is a group

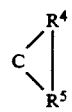

as hereinbefore defined. Suitably R is a cyclopropyl or cyclobutyl group, each optionally substituted by methyl.

Suitably $R^1$ is hydrogen, cyano, methyl or ethyl each optionally substituted by cyano, methoxy, methylthio, chloro, bromo or fluoro. Most suitably $R^1$ is hydrogen, methyl, cyano or trifluoromethyl. Preferably $R^1$ is hydrogen.

Suitably $R^2$ is hydrogen, cyano, methyl or trifluoromethyl. Preferably $R^2$ is hydrogen.

$R^3$ suitably contains between 3 and 12 carbon atoms. Preferably there is only one silyl group present. The sulphur atoms present may be in an oxidised form is desired. Preferably there is a maximum of two sulphur atoms present in $R^3$. Suitably there is a maximum of four and preferably a maximum of three oxygen atoms in $R^3$. Preferably there is only one nitrogen atom present in $R^3$. $R^3$ is suitably a $C_{3-9}$ alkyl, alkenyl or alkynyl group, each of which may be optionally substituted by halo or a group $R^{13}$, or $R^3$ is a substituted phenyl or cyclohexyl group. The group $R^{13}$ is linked to the hydrocarbyl group via a hetero atom of $R^{13}$. Suitable substituents $R^{13}$ for the group $R^{12}$ include alkoxy, alkenyloxy, alkynyloxy, alkoxyalkoxy, acyloxy, alkynyloximino, trialkylsilyl, haloalkoxy, haloalkenyloxy, haloalkynyloxy, alkyloximino, alkoxycarbonyloxy and mono or di-substituted alkylamino groups or a group —$(O)_n$-$S(O)_r(O)_w$ $R^{19}$ wherein $R^{19}$ is a $C_{1-4}$ aliphatic group optionally substituted by halo, n is 0 or 1, r is 0, 1 or 2 and w is 0 or 1, the sum of n, r and w being between 0 and 3. When a silyl group is present this is normally adjacent to an ethynyl group. Preferred substituents $R^{13}$ include alkoxy, alkoxyalkoxy, alkenyloxy, alkynyloxy, haloalkoxy, haloalkenyloxy and haloalkynyloxy. Suitably $R^{12}$ is substituted by up to two substituents $R^{13}$ and preferably $R^{12}$ is unsubstituted or contains one substituent $R^{13}$.

In one suitable embodiment, $R^3$ is a phenyl group substituted at the 3-,4- or 5-positions by one to three substituents each selected from halo, $C_{1-4}$ haloalkyl, cyano, or a group $(C\equiv C)_p R^{20}$ wherein p is 1 or 2 and $R^{20}$ is hydrogen, bromo, chloro, iodo; or $R^{20}$ is an aliphatic group containing up to five carbon atoms optionally substituted by $C_{1-4}$ alkoxy, $C_{1-6}$ alkoxyalkoxy, $C_{1-8}$ acyloxy, halo or hydroxy; or $R^{20}$ is $SiR^{16} R^{17} R^{18}$ wherein $R^{16}$ $R^{17}$ and $R^{18}$ are as hereinbefore defined. When $R^3$ is a substituted phenyl group it is additionally optionally substituted at the 2- and/or 6-positions by fluoro or chloro.

In one preferred embodiment $R^3$ is phenyl substituted at the 3-, 4- or 5- positions by one to three substituents each selected from halo, cyano, $C_{1-4}$ haloalkyl or a group $C\equiv C-R^{21}$ where $R^{21}$ is hydrogen, or methyl or ethyl each optionally substituted by hydroxy, methoxy, ethoxy, acetoxy; or $R^{21}$ is ethynyl, or a silyl group substituted by three $C_{1-4}$ alkyl groups; $R^3$ is additionally optionally substituted at the 2- and/or 6-positions by fluoro or chloro. Preferably $R^3$ is phenyl para substituted by a group —$C\equiv C-R^{22}$ wherein $R^{22}$ is hydrogen.

In a second preferred embodiment $R^3$ is a group —B(-$C\equiv C)Z$, wherein B is a $C_{3-5}$ aliphatic chain optionally containing a double bond and/or an oxygen atom and/or a group $S(O)_q$ wherein q is 0, 1 or 2, and optionally substituted by halo, $C_{1-4}$ alkyl, $C_{1-4}$ haloalkyl, $C_{2-4}$ carbalkoxy or cyano and Z is hydrogen, $C_{1-5}$ alkyl, $C_{1-3}$ alkoxymethyl or a group $SiR^{16} R^{17} R^{18}$ wherein $R^{16}$, $R^{17}$ and $R^{18}$ are as hereinbefore defined.

In a third preferred embodiment $R^3$ is a group -$DZ^1$, wherein D is a group —$CH_2O$— or $CH_2S(O)_q$ wherein q is 0, 1 or 2 or a $C_{2-3}$ aliphatic group each of which may be optionally substituted by one to three halo atoms and $Z^1$ is silyl substituted by three $C_{1-4}$ alkyl groups or $Z^1$ is a group

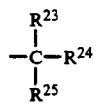

wherein $R^{23}$, $R^{24}$ and $R^{25}$ are the same or different and are each independently selected from halo, cyano, $C_{2-5}$ carbalkoxy, or a $C_{1-4}$ aliphatic group optionally substituted by halo, cyano, $C_{2-5}$ carbalkoxy, $C_{1-4}$ alkoxy or a group $S(O)_q R^{26}$ wherein q is 0, 1 or 2 and $R^{26}$ is $C_{1-4}$ alkyl, or $R^{23}$, $R^{24}$ and $R^{25}$ are selected from $C_{1-4}$ alkoxy or a group $S(O)_z R^{27}$ wherein z is 0, 1 or 2 and $R^{27}$ is $C_{1-4}$ alkyl optionally substituted by fluoro or $R^{23}$ and $R^{24}$ are linked to form a $C_{3-6}$ cycloalkyl ring, or one of $R^{23}$, $R^{24}$ and $R^{25}$ may be hydrogen.

Suitably $R^4$ is oxygen, $CH_2$, $CF_2$ CHMe or $C(Me)_2$. Suitably $R^5$ is $CH_2$, $CF_2$, $C(Me)_2$ or $CH_2CH_2$. Suitably $R^6$ is hydrogen or methyl.

By the term "aliphatic group" is meant an alkyl, alkenyl or alkynyl group.

Most suitably D is a group —$C\equiv C-$ —$CH=CH-$ or —$CH_2CH_2-$.

Preferably $Z^1$ is tertiary butyl, trichloromethyl or 2-methoxyprop-2-yl.

In a fourth preferred embodiment $R^3$ is a group

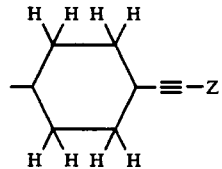

wherein Z is as hereinbefore defined:

A preferred group of compounds of the formula (I) is that in which $R^3$ contains a —$(C\equiv C)$— fragment or terminates in a group $Z^1$ as hereinbefore defined.

4-Cyclobutyl-1-(4-iodophenyl)-2,6,7-trioxabicyclo[2.2.2]octane

4-Cyclobutyl-1-(4-trimethylsilylethynylphenyl)-2,6,7-trioxabicyclo[2.2.2]octane

4-Cyclobutyl-1-[4-(prop-1-ynyl)phenyl]-2,6,7-trioxabicyclo[2.2.2]octane

4-Cyclobutyl-1-(4-ethynylphenyl)-2,6,7-trioxabicyclo[2.2.2]octane

4-Cyclobutyl-1-(hex-5-ynyl)-2,6,7-trioxabicyclo[2.2.2]octane

3-Cyano-4-cyclobutyl-1-(4-ethynylphenyl)-2,6,7-trioxabicyclo[2.2.2]octane

3-Cyano-4-cyclobutyl-1-(hex-5-ynyl)-2,6,7-trioxabicyclo[2.2.2]octane

4-Cyclopropyl-1-(4-iodophenyl)-2,6,7-trioxabicyclo[2.2.2]octane

4-Cyclopropyl-1-(4-trimethylsilylethynyl-phenyl)-2,6,7-trioxabicyclo[2.2.2]octane 4-Cyclopropyl-1-(4-ethnynylphenyl)-2,6,7-trioxabicyclo[2.2.2]octane 4-Cyclopropyl-1-[4-prop-1-ynyl)phenyl]-2,6,7-trioxabicyclo[2.2.2]octane 1-(4-Iodophenyl)-4-(trans-2-methylcyclopropyl)-2,6,7-trioxabicyclo[2.2.2]octane 4-(trans-2-Methylcyclopropyl)-1-(4-trimethylsilylethynylphenyl)-2,6,7-trioxabicyclo[2.2.2]octane 1-(4-Ethynylphenyl)-4-(trans-2-methylcyclopropyl)-2,6,7-trioxabicyclo[2.2.2]octane 4-(trans-2-Methylcyclopropyl)-1-[4-(prop-1-ynyl)-phenyl]-2,6,7-trioxabicyclo[2.2.2]octane 1-(4-Iodophenyl)-4-(1-methylcyclopropyl)-2,6,7-trioxabicyclo[2.2.2]octane 4-(1-Methylcyclopropyl)-1-(4-trimethylsilylethynylphenyl)-2,6,7-trioxabicyclo[2.2.2]octane 1-(4-Ethynylphenyl)-4-(1-methylcyclopropyl)-2,6,7-trioxabicyclo[2.2.2]octane 4-(1-Methylcyclopropyl)-1-[4-(prop-1-ynyl)phenyl]-2,6,7-trioxabicyclo[2.2.2]octane 4-(3-Fluorophenyl-1-(4-iodophenyl)-2,6,7-trioxabicyclo[2.2.2]octane 4-(4-Fluorophenyl)-1-(4-iodophenyl)-2,6,7-trioxabicyclo[2.2.2]octane 4-(3-Fluorophenyl)-1-(4-trimethylsilylethynylphenyl)-2,6,7-trioxabicyclo[2.2.2]octane 4-(4-Fluorophenyl)-1-(4-trimethylsilylethynylphenyl)-2,6,7-trioxabicyclo[2.2.2]octane 1-(4-Ethynylphenyl)-4-(3-fluorophenyl)-2,6,7-trioxabicyclo[2.2.2]octane 1-(4-Ethynylphenyl)-4-(2-fluorophenyl)-2,6,7-trioxabicyclo[2.2.2]octane 1-(4-Ethynylphenyl)-4-(4-fluorophenyl)-2,6,7-trioxabicyclo[2.2.2]octane 4-(3,4-Difluorophenyl)-1-(4-ethynylphenyl)-2,6,7-trioxabicyclo[2.2.2]octane 4-(4-Fluorophenyl)-1-[4-(prop-1-ynyl)phenyl]-2,6,7-trioxabicyclo[2.2.2]octane The compounds of the formula (I) may exist in a number of isomeric forms. The present invention provides individual isomers of compounds of the formula (I) and mixtures thereof. The present invention also encompasses compounds of the formula (I) containing radioisotopes, particularly those in which one carbon atom is $C^{14}$ or one to three hydrogen atoms are replaced by tritium.

In a further aspect, the present invention provides a process for the preparation of a compound of the formula (I). The process for the preparation of a compound of the formula (I) may be any method known in the art for preparing analogous compounds, for example:

(i) when Y, $Y^1$ and $Y^2$ are oxygen: by the cyclisation of a compound of the formula (II):

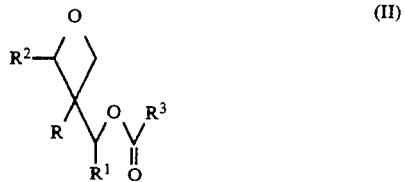

(II)

wherein R to $R^3$ are as hereinbefore defined, in the presence of an acid catalyst. Boron trifluoride etherate is a particularly preferred acid catalyst for this cyclisation which will normally be carried out in an inert solvent, such as a halogenated hydrocarbon, conveniently dichloromethane, at or below ambient temperature, for example between $-100°$ and $50°$ C. and conveniently between $-70°$ and $-25°$ C.

The compounds of the formula (II) may be prepared by the reaction of compounds of the formulae (III) and (IV):

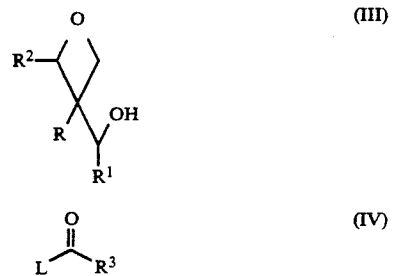

(III)

(IV)

where R to $R^3$ are as hereinbefore defined and L is a leaving group such as halo or hydroxy. This reaction conveniently takes place under conditions well known to those skilled in the art, for example when L is halo in an inert solvent in the presence of base at a non-extreme temperature and when L is hydroxy in an inert solvent in the presence of a condensing agent at a non extreme temperature. When L is halo, halogenated hydrocarbons, such as dichloromethane, are particularly suitable inert solvents and pyridine is a preferred base; when L is hydroxy, dimethylformamide is a suitable solvent, dicyclohexylcarbodiimide is a preferred condensing agent; and the reaction will conveniently be carried out at between $-50°$ and $100°$ C., preferably between $0°$ and $25°$ C.

The compounds of the formula III may be prepared as described in copending European Patent Applications Nos. 211598 and 216624. The compounds of the formula (IV) may be prepared by methods well known to those skilled in the art.

(ii) when Y, $Y^1$ and $Y^2$ are each oxygen or sulphur by the reaction of a compound of the formula (V) with a compound of the formula $(AlkO)_3CR^3$

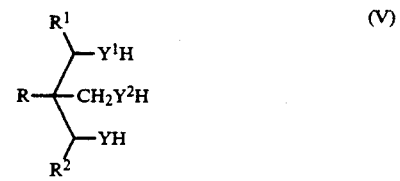

(V)

wherein R to $R^3$, Y, $Y^1$ and $Y^2$ are as hereinbefore defined and Alk is a $C_{1-4}$ alkyl group. The condensation takes place in the presence of an acid catalyst for example a mineral acid such as concentrated hydrochloric acid or boron trifluoride etherate or sulphonic acid resins and/or p-toluenesulphonic acid. The reaction is conveniently carried out without a solvent, but an inert solvent, conveniently toluene or a chlorinated hydrocarbon such as dichloromethane may be added. The reaction can also be carried out in methanol containing hydrogen chloride. The reaction is conveniently carried out at a non-extreme temperature, for example between $-70°$ C. and $150°$ C. and normally between $-10°$ C. and $150°$ C. The compounds of the formula (V) may be prepared as described in European Patent Application No. 216624. Compounds of the formula (V) wherein $Y=Y^1=Y^2=S$ and $R^1=R^2=H$ may also be prepared by the method described by G. R. Franzen and G. Binsch, J. Amer. Chem. Soc., 1973, 95, 175 and D. J. Martin and C. R. Creco, J. Org. Chem., 1968, 33, 1275. The compounds of the formula $(AlkO)_3C R^3$ may be prepared by a general procedure for the synthesis of orthoesters and is described by S. M. McElvain and R. E. Starn, J. Amer. Chem. Soc., 1955, 77, 4571;

(iii) when $Y^2$=sulphur or oxygen and Y and $Y^1$ are sulphur by reaction of a compound of the formula (VI)

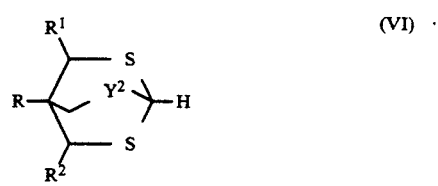

(VI)

with a compound $L^1R^3$ wherein R to $R^3$, are as hereinbefore defined, $Y^2$ is sulphur or oxygen and $L^1$ is a leaving group eg. halo. The reaction is suitably carried out in the presence of a strong base, such as an alkyllithium, in an inert solvent, such as an ether and conveniently tetrahydrofuran at a non-extreme temperature, such as between −70° and 30° C. The compound of the formula (VI) can be prepared by the reaction of the appropriate compound of the formula (V) with HC(OAlk)$_3$ under the conditions described for reaction (ii) above.

By the interconversion of compounds of the formula (I), for example a) when it is desired to prepare a compound of the formula (I) wherein R$^3$ contains a non-terminal C≡C fragment by the reaction of the compound wherein R$^3$ is a group A$^1$C≡CH with a compound A$^2$ hal wherein hal is halogen and A$^1$C≡CA$^2$ is the desired group R$^3$, A$^2$ being other than hydrogen. This reaction is particularly suitable for the preparation of those compounds wherein A$^2$ is a C$_{1-4}$ alkyl group or C$_{2-4}$ carbalkoxy group; or A$^2$ is a substituted silyl group. The reaction is normally carried out in the presence of a strong base, such as an alkyllithium conveniently butyllithium in an inert solvent, such as an ether, for example tetrahydrofuran, at a non-extreme temperature, for example between −50° and 50° C. and conveniently between −10° and 30° C. The starting material, e.g. the unsubstituted alkynylalkyl or alkynylaryl bicycloalkane may be prepared as described above.

(b) when R$^3$ terminates in a C≡CH group by desilylation of a compound of the formula (VII)

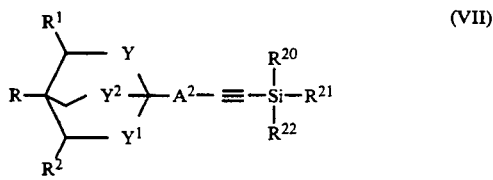

wherein R, R$^1$, R$^2$, R$^{16}$, R$^{17}$, R$^{18}$, Y, Y$^1$ and Y$^2$ are as defined and A$^3$ C≡CH is the desired group R$^3$. This reaction may be carried out by methods well known to those skilled in the art, for example by reaction with tetrabutylammonium fluoride in an ether, such as tetrahydrofuran, at a non-extreme temperature, for example between 0° and 70° C. and conveniently at 25° C.

(c) by the reaction of the corresponding compound which contains iodo or bromo in place of —C≡C—R$^{12}$ or C≡C—R$^{14}$ with a compound HC≡CR$^{12}$ or HC≡CR$^{14}$ wherein R$^{12}$ and R$^{14}$ are as hereinbefore defined. This reaction is carried out in the presence of a suitable palladium catalyst well known to those skilled in the art for this type of reaction, for example bis-triphenylphosphine palladium dichloride, and a catalytic amount of a cuprous halide, such as cuprous iodide when the starting material contains an iodo group and palladium acetate and triphenyl phosphine when the starting material contains a bromo group. The reaction will normally be carried out in the presence of basic solvent such as diethylamine or triethylamine at a non-extreme temperature, for example between −50° and 100° C. and conveniently at room temperature.

It will be apparent to those skilled in the art that some compounds of the formula (I) may be susceptible to degradation under some of the reaction conditions described above, these compounds will be prepared by other methods.

Novel chemical intermediates also form an important aspect of the present invention. Preferred intermediates include those of the formula (II), (V), (VII), (XIV) and (XV).

The compounds of formula (I) may be used to control pests such as arthropods e.g. insect and acarine pests, and helminths, i.e. nematodes. Thus, the present invention provides a method for the control of arthropods and/or helminths which comprises administering to the arthropod and/or helminth or to their environment an arthropodically effective amount of a compound of the formula (I).

The present invention also provides a method for the control and/or eradication of arthropod and/or helminth infestations of animals (including humans) and/or of plants, (including trees) and/or stored products which comprises administering to the animal or locus an effective amount of a compound of the formula (I). The present invention further provides for the compounds of the formula (I) for use in human and veterinary medicine, in public health control and in agriculture for the control of arthropod and/or helminth pests.

The compounds of formula (I) are of particular value in the protection of field, forage, plantation, glasshouse, orchard and vineyard crops, of oranamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus) or beetles (e.g. scolytids, platypodids, lyctids, bostrychids, cerambycids, anobiids).

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of general formula I are of particular value in the control of arthropods or helminths which are injurious to, or spread or act as vectors of diseases in man and domestic animals, for example those hereinbefore mentioned, and more especially in the control of ticks, mites, lice, fleas, midges and biting, nuisance and myiasis flies.

The compounds of Formula (I) may be used for such purposes by application of the compounds themselves or in diluted form in known fashion as a dip, spray, fog, lacquer, foam, dust, powder, aqueous suspension, paste, gel, cream, shampoo, grease, combustible solid, vapourising mat, combustible coil, bait, dietary supplement, wettable powder, granule, aerosol, emulsifiable concentrate, oil suspensions, oil solutions, pressure-pack, impregnated article, pour on formulation or other standard formulations well known to those skilled in the art. Dip concentrates are not applied per se, but diluted with water and the animals immersed in a dipping bath containing the dip wash. Sprays may be applied by hand or by means of a spray race or arch. The animals, soil, plant or surface being treated may be saturated with the spray by means of high volume application or superficially coated with the spray by means of light or ultra low volume application. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material, such as that against which animals rub and transfer the material to their skins. Pour-on formulations are dispensed as a unit of liquid of small volume on to the backs of animals such that all or most of the liquid is retained on the animals.

The compounds of Formula (I) may be prepared either as formulations ready for use on the animals, plants or surface or as formulations requiring dilution prior to application, but both types of formulation comprise a compound of Formula (I) in intimate admixture with one or more carries or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powders and granules and other solid formulations comprise the compound of Formula (I) in intimate admixture with a powdered solid inert carrier for example suitable clays, kaolin, bentonite, attapulgite, absorbent carbon black, talc, mica, chalk, gypsum, tricalcium phosphate, powdered cork, magnesium siliate, vegetable carriers, starch and diatomaceous earths. Such solid formulations are generally prepared by impregnating the solid diluents with solutions of the compound of formula (I) in volatile solvents, evaporating the solvents and, if desired grinding the products so as to obtain powders and, if desired, granulating, compacting or encapsulating the products.

Sprays of a compound of Formula (I) may comprise a solution in an organic solvent (e.g. those listed below) or emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates. Cationic emulsifiers include benzalkonium chloride and quaternary ammonium ethosuphates.

Amphoteric emulsifiers include carboxymethylated oleic imidazoline and alkyl dimethyl betain.

Vaporising mats normally comprise cotton and cellulose mix compressed into a board of approximately $35 \times 22 \times 3$ mm dimensions, treated with up to 0.3 ml of concentrate comprising the active ingredient in an organic solvent and optionally an antioxidant, dye and perfume. The insecticide is vaporised using a heat source such as an electrically operated mat heater.

Combustible solids normally comprise of wood powder and binder mixed with the active ingredient and formed into shaped (usually coiled) strips. Dye and fungicide may also be added. Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium. An avian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body. Suitably the plastics material is a polyvinyl chloride (PVC).

The concentration of the compound of Formula (I) to be applied to an animal, premises or outdoor areas will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% w/w except for undiluted formulations such as pour-on formulations which in general will be deposited at a concentration in the range from 0.1 to 20.0% and preferably 0.1 to 10%. The amount of compound to be applied to stored products in general will lie in the range of from 0.1 to 20 ppm. Space sprays may be applied to give an average initial concentration of 0.001 to 1 mg of compound of formula (I) per cubic meter of treated space.

The compounds of formula (I) are also of use in the protection and treatment of plant species, in which case an effective insecticidal, acaricidal or nematocidal amount of the active ingredient is applied. The application rate will vary according to the compound chosen, the nature of the formulation, the mode of application, the plant species, the planting density and likely infestation and other like factors but in general, a suitable use rate for agricultural crops is in the range 0.001 to 3 kg/Ha and preferably between 0.01 and 1 kg/Ha. Typical formulations for agricultural use contain between 0.0001% and 50% of a compound of formula (I) and conveniently between 0.1 and 15% by weight of a compound of the formula (I).

Dusts, greases, pastes and aerosol formulations are usually applied in a random fashion as described above and concentrations of 0.001 to 20% w/v of a compound of Formula (I) in the applied formulation may be used.

The compounds of formula (I) have been found to have activity against the common housefly (*Musca domestica*). In addition, certain compounds of formula (I) have activity against other arthropod pests including *Myzus persicae, Tetranychus urticae, Plutella xylostella,* Cule spp. *Tribolium castaneum, Sitophilus granarius, Periplaneta amiercana* and *Blattella germanica.* The compounds of formula (I) are thus useful in the control of arthropods e.g. insects and acarines in any environment where these constitute pests, e.g. in agriculture, in animal husbandry, in public health control and in domestic situations.

Insect pests include members of the orders Coleoptera (e.g. Anobium, Ceutorhynchus, Rhynchophorus, Cosmopolites, Lissorhoptrus, Meligethes, hypothenemus, Hylesinus, Acalymma, Lema, Psylliodes, Leptinotarsa, Gonocephalum, Agriotes, Dermolepida, Heteronychus, Phaedon, Tribolium, Sitophilus, Diabrotica, Anthonomus or Anthrenus spp.) Lepidoptera (e.g. Ephestia, Mamestra, Earias, Pectinophora, Ostrinia, Trichoplusia, Pieris, Laphygma, Agrotis, Amathes, Wiseana, Tryorysa, Diatraea, Sporganothis, Cydia, Archips, Plutella, Chilo, Heliothis, Spondoptera or Tineola spp.), Diptera (e.g. Musca, Aedes, Anopheles, Culex. Glossina, Simulium, Stomoxys, Haematobia, Tabanus, Hydrotaea, Lucilia, Chrysomia, Callitroga, Dermatobia, Gasterophilus, Hypoderma, Hylemyia, Atherigona, Chlorops, Phytomyza, Ceratitis, Liriomyza and Melophagus spp.), Phthiraptera (Malophaga e.g. Damalina spp. and Anoplura e.g. Linognathus and Haematopinus spp.), Hemiptera (e.g. Aphis, Bemisia, Phorodon, Aeneolamia, Empoasca, Parkinsiella, Pyrilla, Aonidiella, Coccus, Pseudococus, Helopeltis, Lygus, Dysdercus, Oxycarenus, Nezara, Aleurodes, Triatoma, psylla, Myzus, Megoura, Phylloxera, Adelyes, Niloparvata, Nephrotetix or Cimex spp.), Orthoptera (e.g. Locusta, Gryllus, Schistocerca or Acheta spp.), Dictyoptera (e.g. Blattella, Periplaneta or Blatta spp.), Hymenoptera (e.g. Athalia, Cephus, Atta, Solenopsis or Monomorium spp.), Isoptera (e.g. Odontotermes and Reticulitermes spp.), Siphonaptera (e.g. Ctenocephalides or Pulex spp.), Thysanura (e.g. Lepisma spp.), Dermaptera (e.g. Forficula spp.), Pscoptera (e.g. Peripsocus spp.) and Thysanoptera (e.g. *Thrips tabaci*).

Acarine pests include ticks, e.g. members of the genera Boophilus, Ornithodorus, Rhipicephalus, Amblyomma, Hyalomma, Ixodes, Haemaphysalis, Dermacentor and Anocentor, and mites and manges such as Acarus, Tetranychus, Psoroptes, Notoednes, Sarcoptes, Psorergates, Chorioptes, Eutrombicula, Demodex, Panonychus, Bryobia, Eriophyes, Blaniulus, Polyphagotarsonemus, Scutigerella, and Oniscus spp.

Nematodes which attack plants and trees of importance to agriculture, forestry, horticulture either directly or by spreading bacterial, viral, mycoplasma or, fungal diseases of the plants, include root-knot nematodes such as Meloidogyne spp. (e.g. *M. incognita*); cyst nematodes such as Globodera spp. (e.g. *G. rostochiensis*); Heterodera spp. (e.g. *H. avenae*); Radopholus spp. (e.g. *R. similis*); lesion nematodes such as Pratylenchus spp. (e.g. *P. pratensis*); Belonolaimus spp. (e.g. *B. gracilis*); Tylenchulus spp. (e.g. *T. semipenetrans*); Rotylenchulus spp. (e.g. *R. reniformis*); Rotylenchus spp. (e.g. *R. robustus*); Helicotylenchus spp. (e.g. *H. multicinctus*); Hemicycliophora spp. (e.g. *H. gracilis*); Criconemoides spp. (e.g. *C. similis*); Trichodorus spp. (e.g. *T. primitivus*); dagger nematodes such as Xiphinema spp. (e.g. *X. diversicaudatum*), Longidorus spp (e.g. *L. elongatus*); Hoplolaimus spp. (e.g. *H. coronatus*); Aphelenchoides spp. (e.g. *A. ritzema-bosi, A. besseyi*); stem and bulb eelworms such as Ditylenchus spp. (e.g. *D. dipsaci*).

Compounds of the invention may be combined with one or more other pesticidally active ingredients (for example pyrethroids, carbamates and organophosphates) and/or with attractants, repellents, bacteriocides, fungicides, nematocides, anthelmintics and the like. Furthermore, it has been found that the activity of the compounds of the invention may be enhanced by the addition of a synergist or potentiator, for example: one of the oxidase inhibitor class of synergists, such as piperonyl butoxide or propyl 2-propynylphenylphosphonate; a second compound of the invention; or a pyrethroid pesticidal compound. When an oxidase inhibitor synergist is present in a formula of the invention, the ratio of synergist to compound of Formula (I) will be in the range 25:1–1:25 e.g. about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin) and organic or inorganic bases e.g. trialkylamines such as triethylamine which can act as basic stabilises and as scavengers.

| Formulations | |
|---|---|
| 1. Emulsifiable Concentrate | |
| Compound of formula (I) | 10.00 |
| Alkyl phenol ethoxylate* | 7.50 |
| Alkyl aryl sulphonate* | 2.50 |
| $C_{8-13}$ aromatic solvent | 80.00 |
| | 100.00 |
| 2. Emulsifiable Concentrate | |
| Compound of formula (I) | 10.00 |
| Alkyl phenol ethoxylate* | 2.50 |
| Alkyl aryl sulphonate* | 2.50 |
| Ketonic solvent | 64.00 |
| $C_{8-13}$ aromatic solvent | 18.00 |
| Antioxidant | 3.00 |

| Formulations | |
|---|---|
| 3. Wettable Powder | 100.00 |
| Compound of formula (I) | 5.00 |
| C$_{8-13}$ aromatic solvent | 7.00 |
| C$_{18}$ aromatic solvent | 28.00 |
| China clay | 10.00 |
| Alkyl aryl sulphonate* | 1.00 |
| Naphthalene sulphonic acid* | 3.00 |
| Diatomaceous earth | 46.00 |
| | 100.00 |
| 4. Dust | |
| Compound of formula (I) | 0.50 |
| Talc | 99.50 |
| | 100.00 |
| 5. Bait | |
| Compound of formula (I) | 0.5 |
| Sugar | 79.5 |
| Paraffin wax | 20.0 |
| | 100.00 |
| 6. Emulsion Concentrate | |
| Compound of formula (I) | 5.00 |
| C$_{8-13}$ aromatic solvent | 32.00 |
| Cetyl alcohol | 3.00 |
| Polyoxyethylene glycerol monooleate* | 0.75 |
| Polyoxyethylene sorbitan esters* | 0.25 |
| Silicone solution | 0.1 |
| Water | 58.9 |
| | 100.00 |
| 7. Suspension Concentrate | |
| Compound of formula (I) | 10.00 |
| Alkyl aryl ethoxylate* | 3.00 |
| Silicone solution | 0.1 |
| Alkane diol | 5.0 |
| Fumed silica | 0.50 |
| Xanthan gum | 0.20 |
| Water | 80.0 |
| Buffering agent | 1.2 |
| | 100.00 |
| 8. Microemulsion | |
| Compound of formula (I) | 10.00 |
| Polyethylene glycerol monooleate* | 10.00 |
| Alkane diol | 4.00 |
| Water | 76.00 |
| | 100.00 |
| 9. Water Dispersible Granules | |
| Compound of formula (I) | 70.00 |
| Polyvinyl pyrrolidine | 2.50 |
| Alkyl aryl ethoxylate | 1.25 |
| Alkyl aryl sulphonate | 1.25 |
| China clay | 25.00 |
| | 100.00 |
| 10. Granules | |
| Compound of formula (I) | 2.00 |
| Alkyl phenol ethoxylate* | 5.00 |
| Alkyl aryl sulphonate* | 3.00 |
| C$_{8-13}$ aromatic solvent | 20.00 |
| Kieselguhr granules | 70.00 |
| | 100.00 |
| 11. Aerosol (pressure pack) | |
| Compound of formula (I) | 0.3 |
| Piperonyl butoxide | 1.5 |
| C$_{8-13}$ saturated hydrocarbon solvent | 58.2 |
| Butane | 40.0 |
| | 100.00 |
| 12. Aerosol (pressure pack) | |
| Compound of formula (I) | 0.3 |
| C$_{8-13}$ saturated hydrocarbon solvent | 10.0 |
| Sorbitan monooleate* | 1.0 |
| Water | 40.0 |
| Butane | 48.7 |
| | 100.00 |
| 13. Aerosol (pressure pack) | |
| Compound of formula (I) | 1.00 |
| CO$_2$ | 3.00 |
| Polyoxyethylene glycerol monooleate* | 1.40 |
| Propanone | 38.00 |
| Water | 56.60 |
| | 100.00 |

| Formulations | |
|---|---|
| 14. Lacquer | |
| Compound of formula (I) | 2.50 |
| Resin | 5.00 |
| Antioxidant | 0.50 |
| High aromatic white spirit | 92.0 |
| | 100.00 |
| 15. Spray (ready to use) | |
| Compound of formula (I) | 0.10 |
| Antioxidant | 0.10 |
| Odourless kerosene | 99.8 |
| | 100.00 |
| 16. Potentiated Spray (ready to use) | |
| Compound of formula (I) | 0.10 |
| Piperonyl butoxide | 0.50 |
| Antioxidant | 0.10 |
| Odourless kerosene | 99.30 |
| | 100.00 |
| 17. Microencapsulated | |
| Compound of formula (I) | 10.0 |
| C$_{8-13}$ aromatic solvent | 10.0 |
| Aromatic di-isocyanate# | 4.5 |
| Alkyl phenol ethoxylate* | 6.0 |
| Alkyl diamine# | 1.0 |
| Diethylene triamine | 1.0 |
| Concentrated hydrochloric acid | 2.2 |
| Xanthan gum | 0.2 |
| Fumed silica | 0.5 |
| Water | 64.6 |
| | 100.00 |

*Surfactant
react to form the polyurea walls of the microcapsule
Antioxidant could be any of the following individually or combined
Butylated hydroxytoluene
Butylated hydroxyanisole
Vitamin C (ascorbic acid)

The following examples illustrate, in a non-limiting manner, preferred aspects of the invention. All temperatures are in degrees.

EXAMPLE 1

4-Cyclobutyl-1-(4-iodophenyl)-2,6,7-trioxabicyclo[2.2.2]octane (i) Sodium (10.3 g, 0.44 mmol) was dissolved in dry ethanol (300 ml) under a nitrogen atmosphere and to the cooled solution (0° C.) was added diethyl malonate (71 g, 0.44 mmol). After stirring for 15 minutes cyclobutyl bromide (60 g, 0.44 mmol) was added and the solution was heated to reflux overnight. The cooled mixture was evaporated and the residue was partitioned between water and ether. The ether layer was separated, dried over anhydrous magnesium sulphate and evaporated. The residue was distilled to give diethyl cyclobutylmalonate (40 g, 42%) (bp. 74°–75° C. at 0.5 mm Hg).

(ii) To a stirred solution of diethyl cyclobutylmalonate (40 g, 0.19 mmol) in dry THF (100 ml) at 0° C. under nitrogen atmosphere was added carefully sodium hydride (4.8 g, 0.2 mmol). The stirred mixture was allowed to warm to room temperature and was then heated to reflux for 1 hour. To the cooled solution was added benzylchloromethyl ether (31.3 g, 0.2 mol) and the mixture was heated to reflux overnight. The cooled solution was partitioned between water and ether and the ether layer was separated, washed with water, dried over anhydrous magnesium sulphate and evaporated to leave diethyl 2-benzyloxymethyl-2-cyclobutylmalonate as an oil (71 g) which was not purified further.

(iii) A solution of diethyl 2-benzyloxymethyl-2-cyclobutylmalonate (65 g, 0.19 mol) in dry ether (50 ml) was added dropwise to a stirred suspension of lithium aluminium hydride (11.5 g, 0.3 mol) in dry ether (200 ml) at 0° C. under a nitrogen atmosphere. After the addition, the solution was heated to gentle reflux for 1 hour, allowed to cool and an excess of saturated aqueous ammonium chloride was added. Stirring was continued overnight and the resulting mixture was filtered and the solids washed with ether. The filtrate was extracted with ether, the ether extracts were combined, dried over anhydrous magnesium sulphate and evaporated to leave 2-benzyloxymethyl-2-cyclobutylpropane-1,3-diol (49 g) as an oil.

(iv) A solution of 2-benzyloxymethyl-2-cyclobutyl-propane-1,3-diol (49 g, 0.2 mol) in dry ether (200 ml) was added to liquid ammonia (450 ml) stirred at −70° C. Sodium pellets (14 g, 0.6 mol) were added and the stirred mixture was allowed to warm to −33° C. over 2 hours. Ammonium chloride (35 g, 0.65 mol) was added and the ammonia was allowed to evaporate overnight. The solid residue was extracted with ether, the extracts were combined, filtered and evaporated to leave 2-cyclobutyl-2-hydroxymethylpropane-1,3-diol as an oil (27.9 g, 87%) which was purified on a silica column eluting with chloroform then increasing amounts of chloroform:methanol (up to 9:1 v/v).

(v) A mixture of 2-cyclobutyl-2-hydroxymethylpropane-1,3-diol (6.7 g, 42 mmol), diethyl carbonate (5.5 g, 46 mmol) and potassium hydroxide (0.1 g in 5 ml dry ethanol) was heated to reflux under nitrogen for 15 minutes. Ethanol was then distilled off at atmospheric pressure and the residue distilled under reduced pressure. 3-Cyclobutyl-3-hydroxymethyloxetane was obtained as a colourless liquid (4.3 g, 73%) bp 130°-160° C. at 30 mm Hg.

(vi) To a stirred solution of 3-cyclobutyl-3-hydroxymethyloxetane (2.84 g, 20 mmol) in dry dichloromethane (40 ml) and pyridine (3 ml) at 0° C. under nitrogen was added a solution of 4-iodobenzoyl chloride (5.33 g, 20 mmol) in dry dichloromethane (10 ml). The solution was stirred overnight at room temperature, washed with water, dried over anhydrous sodium sulphate and evaporated. (3-Cyclobutyloxetan-3-yl)methyl 4-iodobenzoate was obtained as a white solid (7.42 g, 99%) which was not purified further.

(vii) To a stirred solution of (3-cyclobutyloxetan-3-yl)methyl 4-iodobenzoate (7.42 g, 20 mmol) in dry dichloromethane (80 ml) at −70° C. under nitrogen atmosphere was added boron trifluoride etherate (2 ml). The solution was allowed to warm to room temperature, stirred overnight and then quenched with dry triethylamine (3 ml). The mixture was evaporated to dryness, partitioned between water and dichloromethane and the organic layer was separated, dried over anhydrous potassium carbonate and evaporated. The residue was chromatographed on basic alumina. Elution with hexane: dichloromethane (9:1 v/v) gave 4-cyclobutyl-1-(4-iodophenyl)-2,6,7-trioxabicyclo[2.2.2]octane (2.8 g, 38%) as white crystals.

Using the above procedure and starting from hept-6-ynoyl chloride (88306718.3) instead of 4-iodobenzoyl chloride, 4-cyclobutyl-1-(hex-5-ynyl)-2,6,7-trioxabicyclo[2.2.2]octane was prepared.

Using the above methodology the following compounds were also prepared:

4-Cyclopropyl-1-(4-iodophenyl)-2,6,7-trioxabicyclo[2.2.2]octane 1-(4-Iodophenyl)-4-(trans-2-methylcyclopropyl)-2,6,7-trioxabicyclo[2.2.2]octane.

1-(4-Iodophenyl)-4-(1-methylcyclopropyl)-2,6,7-trioxabicyclo[2.2.2]octane.

4-(3-Fluorophenyl)-1-(4-iodophenyl)-2,6,7-trioxabicyclo[2.2.2]octane.

4-(2-Fluorophenyl)-1-(4-iodophenyl)-2,6,7-trioxabicyclo[2.2.2]octane.

4-(2-Fluorophenyl)-1-(4-iodophenyl)-2,6,7-trioxabicyclo[2.2.2]octane.

The required cyclopropyl malonate ester starting materials were prepared as follows:

Cyclopropanecarbonyl chloride (36 g, 0.34 mol) was added dropwise to a stirred solution of ethyl diazoacetate (86.2 g, 0.76 mol) in dry ether (500 ml) at 0° C. under a nitrogen atmosphere. The mixture was allowed to warm to room temperature then was stirred for 1 day, heated to gentle reflux for 2 days, then left to stand at room temperature for 5 days. Evaporation of the mixture followed by distillation afforded ethyl 3-cyclopropyl-2-diazo-3-oxo-propanoate (27.4 g, 44%) bp 85°-90° at 1 mm Hg).

A mixture of the above diazoester (12.6 g, 70 mmol) and silver oxide (100 mg) in anhydrous toluene (12 ml) was heated to reflux under an atmosphere of carbon dioxide for 4 hours. The cooled solution was evaporated and the residue was distilled into a flask containing dry ethanol (15 ml) cooled to −70° C. The ketene distilled slowly, bp 70°-90° C. at 1 mm hg. The ethanolic solution was allowed to warm to room temperature and was then evaporated to leave diethyl cyclopropylmalonate (9.8 g, 71%) (bp 75°-80° C. at 1 mm Hg).

The following data for intermediate triols are also included:

2-cyclopropyl-2-hydroxymethylpropane-1,3-diol was a colourless solid, m.pt. 57°-58° C.

2-hydroxymethyl-2-(trans 2-methylcyclopropyl)propane-1,3-diol was an oil.

2-hydroxymethyl-2-(1-methylcyclopropyl)propane-1,3-diol was a colourless solid, m.pt. 79°-81° C.

2-(3-Fluorophenyl)-2-hydroxymethylpropane-1,3-diol was prepared as follows:

(i) To a stirred suspension of lithium aluminium hydride (25 g, 0.65 mol) in dry ether (300 ml) at 0° C. was added dropwise 3-fluorophenylacetic acid (50 g, 0.32 mol, Lancaster Synthesis). After the addition the mixture was heated to reflux for 2 hours, then stirred overnight at room temperature. Saturated aqueous ammonium chloride (200 ml) was added and the mixture was filtered and the solids washed with ether. The ether layer was separated, dried over anhydrous magnesium sulphate and evaporated. Distillation of the residue afforded 2-(3-fluorophenyl)ethanol (43.05 g, 95%), bp 91°-94° at 2 mmHg, NMR δ 7.3 (1H, m), 7.05–6.9 (3H, m), 3.85 (2H,t), 2.85 (2H,t), 2.0 (1H,s).

(ii) To a stirred suspension of pyridinium chlorochromate (75.5 g, 0.35 mol) in dry dichloromethane (300 ml) under a nitrogen atmosphere was added 2-(3-fluorophenyl)ethanol (43 g, 0.31 mol) dropwise. After the addition the mixture was stirred for 1 hour, allowed to stand overnight then poured down a florisil column. The column was washed with ether and the combined filtrate and washings were evaporated to leave the crude 3-fluorophenyl acetaldehyde as an unstable liquid which was not purified further (34 g), NMR δ 9.75 (1H, t), 7.3 (1H, m), 7.05–6.9 (3H, m), 3.7 (2H, d).

(iii) A mixture of 3-fluorophenylacetaldehyde (34 g crude), formalin (250 ml) and aqueous sodium hydroxide (12 g in 270 ml H₂O) was stirred vigorously at 50° C.

for three days. The resultant solution was evaporated to dryness and the residue was washed thoroughly with isopropanol. Filtration of the isopropanol suspension followed by evaporation of the filtrate afforded a residue which was heated gradually at 0.5 mmHg up to 100° C. to remove volatiles. The cooled residue was purified on a silica column and elution with chloroform-methanol (9:1 v/v) gave 2-(3-fluorophenyl)-2-hydroxymethylpropane-1,3-diol as a yellow oil (5.8 g) NMR δ 7.3 (3H m), 6.9 (1H, m), 3.95 (6H, s), 3.9 (3H, broad).

In an analogous manner the following intermediate triols were prepared:

2-(2-fluorophenyl)-2-hydroxymethylpropane-1,3-diol (oil)
2(4-fluorophenyl)-2-hydroxymethylpropane-1,3-diol (m.pt. 73°-75° C.).

EXAMPLE 2

3-Cyano-4-cyclobutyl-1-(4-iodophenyl)-2,6,7-trioxabicyclo[2.2.2] octane (i) To a stirred suspension of pyridinium chlorochromate (10 g, 45 mmol) in dry dichloromethane (100 ml) was added 3-cyclobutyl-3-hydroxymethyloxetane (5 g, 35 mmol). The mixture was stirred for 2 hours, diluted with diethylether and then purified on a florisil column with an ether rinse. Evaporation afforded 3-cyclobutyl-3-formyloxetane (3.72 g, 75%) as a liquid.

(ii) To a stirred solution of 3-cyclobutyl-3-formyloxetane (2.0 g, 14.3 mmol) and 4-iodobenzoyl chloride (5.2 g, 20 mmol) in ether (70 ml) at 0° C. was added a solution of sodium cyanide (2.5 g) in water (2 ml). The solution was stirred at room temperature overnight, then washed with water and the organic layer was dried over anhydrous magnesium sulphate and evaporated. The residue was chromatographed on silica pre-treated with hexane containing 1% triethylamine, eluting with hexane:dichloromethane (9:1 v/v increasing up to 3:7 v/v. 1-Cyano-1(3-cyclobutyloxetan-3yl) methyl 4-iodobenzoate was obtained, 2.35 g, 42%).

(iii) Boron trifluoride etherate (1 ml) was added to a stirred solution of 1-cyano-1(3-cyclobutyloxetan-3-yl)methyl 4-iodobenzoate (2.3 g, 5.8 mmol) in dry dichloromethane (30 ml) at −70° C. under a nitrogen atmosphere. The solution was allowed to warm to room temperature and was stirred overnight. Triethylamine (1 ml) was added, the solution was evaporated to dryness to leave a gum which was partitioned between water and dichloromethane. The organic layer was separated, dried over anhydrous potassium carbonate and evaporated. The residue was chromatographed on basic alumina, eluting with hexane:dichloromethane (4:1 v/v) to give 3-cyano-4-cyclobutyl-1(4-iodophenyl)-2,6,7-trioxabicyclo[2.2.2]octane as a white solid (1.05 g, 46%).

Using the above methodology and starting from hept-6-ynoyl chloride instead of 4-iodobenzoyl chloride, 3-cyano-4-cyclobutyl-1-(hex-5ynyl)-2,6,7-trioxabicyclo[2.2.2]octane was prepared.

EXAMPLE 3

4-Cyclobutyl-1-(4-prop-1-ynylphenyl)-2,6,7-trioxabicyclo[2.2.2]octane

A solution of 4-cyclobutyl-1(4-iodophenyl)2,6,7-trioxabicyclo-[2.2.2]octane (Compound 1) (650 mg, 1.75 mmol), bis(triphenylphosphine) palladium (II) chloride (30 mg) and cuprous iodide (10 mg) in dry diethylamine (40 ml) was stirred at room temperature. Propyne gas was bubbled through the solution for twenty minutes and stirring continued overnight. The solution was evaporated, and the residue was partitioned between water and ether. The organic layer was dried over anhydrous potassium carbonate and evaporated to leave a solid which was purified on basic alumina, elution with hexane:dichloromethane (9:1 v/v) gave 4-cyclobutyl-1-(4-prop-1-ynylphenyl)-2,6,7-trioxabicyclo[2.2.2]octane as a while solid (400 mg, 81%).

Using the above methodology the following compounds were also prepared:

4-Cyclopropyl-1-(4-prop-1ynylphenyl)-2,6,7-trioxabicyclo[2.2.2]octane.
4-(trans-2-Methylcyclopropyl)-1-(4-prop-1-ynylphenyl)-2,6,7-trioxabicyclo[2.2.2]octane.
4-(1-Methylcyclopropyl)-1-(4-prop-1-ynylphenyl)2,6,7-trioxabicyclo[2.2.2]octane.
4-(4-Fluorophenyl)-1-(4-prop-1-ynylphenyl)-2,6,7-trioxabicyclo[2.2.]octane.

EXAMPLE 4

4-Cyclobutyl-1-(4-ethynylphenyl)-2,6,7-trioxabicyclo[2.2.2]octane (i) A solution f 4-cyclobutyl-1-(4-iodophenyl)-2,6,7-trioxabicyclo [2.2.2]octane (1.5 g, 4 mmol), trimethylsilylacetylene (1 ml), bis(triphenylphosphine) palladium (II) chloride (30 mg) and cuprous iodide (10 mg) in dry diethylamine (30 ml) under a nitrogen atmosphere was stirred overnight. The solution was evaporated and the residue partitioned between water and ether. The organic layer was dried over anhydrous magnesium sulphate and evaporated to leave 4-cyclobutyl-1(4-trimethylsilyethynylphenyl)-2,6,7-trioxabicyclo[2.2.2octane as brown flakes (1.38 g, 100%).

(ii) To a stirred solution of 4-cyclobutyl-1-(4-trimethylsilylethynylphenyl)2,6,7-trioxabicyclo[2.2.2]octane (Compound 2) (1.3 g, 3.8 mmol) in dry THF (30 ml) under nitrogen atmosphere was added tetra-butylammonium fluoride (4 ml of 1M solution in THF). The mixture was stirred for one hour, evaporated to dryness and the residue partitioned between water and dichloromethane. The organic layer was separated, dried over anhydrous potassium carbonate and evaporated to leave a residue. Purification on a basic alumina column, eluting with hexane: dichloromethane (9:1 v/v) gave 4-cyclobutyl-1-(4-ethynylphenyl)-2,6,7-trioxabicyclo [2.2.2]octane as a white solid (800 mg, 78%).

Using the above methodology, and starting from the appropriate 1-(4-iodophenyl)bicyclo[2.2.2]octane, the following compound were also prepared:

3-Cyano-4-cyclobutyl-1(4-trimethylsilylethynylpheny)2,6,7-trioxabicyclo[2.2.2]octane.
3-Cyano-4-cyclobutyl-1-(4-ethynylphenyl)-2,6,7-trioxabicyclo [2.2.2]octane.
4-Cyclopropyl-1(4-trimethylsilylethynylpheny)-2,6,7-trioxabicyclo[2.2.2]octane.
4-Cyclopropyl-1-(4-ethynylphenyl)-2,6,7-trioxabicyclo[2.2.2]octane.
4-(trans-2-Methylcyclopropyl)-1-(4-trimethylsilyethynylphenyl)-2,6,7-trioxabicyclo[2.2.2]octane.
1-(4-Ethynylphenyl)-4-trans-2-methcyclopropyl)-2,6,7-trioxabicyclo[2.2.2]octane.
4-(1-Methylcyclopropyl)-1-(4-trimethylsilyethylnylphenyl)2,6,7-trioxabicyclo[2.2.2]octane.

1-(4-Ethynylphenyl)-4-(1-methylcyclopropyl)2,6,7-trioxabicyclo[2.2.2]octane.

4-(3-Fluorophenyl)-4-trimethylsilyethynylphenyl)-2,6,7-trioxabicyclo[2.2.2]octane.

1-(4-Ethynylphenyl)-4(3-fluorophenyl)-2,6,7-trioxabicyclo [2.2.2]octane.

4-(2-Fluorophenyl)-1-(4-trimethylsilyethynylphenyl)-2,6,7 -trioxabicyclo[2.2.2]octane.

1(4-Ethynylphenyl)-4-(2-fluorophenyl)-2,6,7-trioxabicyclo [2.2.2]octane.

4-(4-Fluorophenyl)-1-(4-trimethylsilyethynylphenyl)-2,6,7-trioxabicyclo[2.2.2]octane.

1-(4-Ethynylphenyl)-4-(4-fluorophenyl)-2,6,7-trioxabicyclo [2.2.2]octane.

EXAMPLE 5

1-(4-Chlorophenyl)-4-(4-fluorophenyl)-2,6,7-trioxabicyclo[2.2.2]octane

A mixture of 2-(4-fluorophenyl)-2-hydroxymethylpropane-1,3-diol (1.0 g, 5 mmol), trimethyl 4-chloroorthobenzoate (1.1. g, 5 mmol) and para-toluene sulphonic acid (10 mg) was heated at 140° C. until methanol no longer distilled over. The residue was purified on a basic alumina column, elution with hexane-dichloromethane (4:1 v/v) gave 1-(4-chlorophenyl)4-(4-fluorophenyl)-2,6,7trioxabicyclo[2.2.2]octane (250 mg, 16%) as a white solid, (mp 251°-252° C.).

1(4-Chlorophenyl)-4-2-fluorophenyl)-2,6,7-trioxabicyclo[2.2.2]octane was prepared in an analogous manner from 2-(2-fluorophenyl)-2-hydroxymethylpropane-1,3-diol.

EXAMPLE 6

4-(3,4Difluorophenyl)-1-(4-ethynylphenyl)-2,6,7-trioxabicyclo[2.2.2]octane (i) 3,4-Difluorobenzoyl chloride (75 g, 0.43 mol - Aldrich) was added dropwise to a stirred solution of ethyl diazoacetate (100 g, 0.88 mol) in dry diethyl ether (300 ml) at 0° C. under a nitrogen atmosphere. The mixture was allowed to warm to room temperature then was stirred for 1 day, heated to gentle reflux for 2 days then left to stand at room temperature for 5 days. Evaporation of the mixture followed by distillation up to 45° C. (1 mm Hg) removed by-products (the residue of diazoester was not distilled further but was used directly in the next stage) and ethyl 2-diazo-3-(3,4-difluorophenyl)-3-oxo-propanoate (63 g, 58%) was obtained as a yellow liquid Nmr $\delta$7.5–7.4 (2H,m), 7.2 (1H,m), 4.25 (2H, q), 1.3 (3H,t).

A mixture of the above diazoester (63 g, 0.25 mol) and silver oxide (600 mg) in anhydrous toluene (75 ml) was heated to reflux under an atmosphere of carbon dioxide for 4 hours. The cooled solution was evaporated and the residue was distilled into a flask containing dry ethanol (75 ml) cooled to −70° C. The ketene distilled slowly (bp 80°–135° C., 0.5 mm, Hg). The ethanol solution was allowed to warm to room temperature and was then evaporated to leave diethyl 3,4-difluorophenylmalonate as a yellow liquid (18.6 g, 28%) Nmr $\delta$7.3 (1H,m), 7.1 (2H,m), 4.55 (1H,s), 4.2 (4H,m), 1.25 (6H,t).

(ii) To a stirred solution of diethyl 3,4-difluorophenylmalonate (13 g, 48 mmol) in dry tetrahydrofuran (100 ml) at 0° C. under a nitrogen atmosphere was added sodium hydride (1.5 g, 50 mmol) of 80% oil dispersion). The mixture was allowed to warm to room temperature and then heated to reflux for 1hour. To the cooled mixture was added 4-methoxybenzyl chloromethyl ether (9.5 g, 51 mmol ref. Synthesis, 1983, 762) and reflux was continued overnight. The cooled mixture was partitioned between water and diethyl ether, the organic layer was separated, dried over anhydrous magnesium sulphate and evaporated to leave diethyl 2-(3,4-difluorophenyl)-2(4-methoxybenzyloxymethyl)-malonate as a yellow oil Nmr $\delta$7.35 (1H,m), 7.2 (2H,d), 7.15–7.00 (2H,m), 6.85 (2H,d), 4.45 (2H,s), 4.20 (4H,q), 4.10 (2H,s), 3.80 (3H,s), 1.25 (6H,t).

(iii) A solution of diethyl 2-(3,4-difluorophenyl)-2-(4-methoxybenzyloxymethyl) malonate (22 g, 50 mmol) in dry diethyl ether (50 ml) was added dropwise to a stirred suspension of lithium aluminium hydride (3.8 g, 100 mmol) in dry diethyl ether (250 ml) at 0° C. under a nitrogen atmosphere. After the addition the solution was heated to gentle reflux for 1 hour, allowed to cool and an excess of saturated aqueous ammonium chloride was added. Stirring was continued overnight and the resulting mixture was filtered and the solids washed with diethyl ether. The filtrate was extracted with diethyl ether, the ether extracts combined, dried over anhydrous magnesium sulphate and evaporated to leave 2-(3,4-difluorophenyl)-2-methoxybenzyloxymethyl)-propane-1,3-diol as a yellow oil (16.5 g, 94%) Nmr $\delta$7.3–7.10 (5H,m), 6.85 (2H,d), 4.45 (2 H, s), 3.9 (4H,m), 3.80 (3H,s), 3.75 (2H,s), 2.35 (2H, broad).

(iv) 2-(3,4-Difluorophenyl)-2-(4-methoxybenzyloxymethyl)propane-1,3-diol (16.5 g, 50 mmol), acetone (7.5 ml) and p-toluene sulphonic acid (100 mg) were heated to reflux in benzene (100 ml) and water was removed using Dean and Stark apparatus. After refluxing overnight the cooled solution was washed with saturated aqueous sodium bicarbonate solution and was dried over anhydrous magnesium sulphate. Evaporation gave 2,2-dimethyl-5-(3,4-difluorophenyl)-5-(4-methoxybenzyloxymethyl)-1,3-dioxane as a yellow oil (17.7 g, 97%, Nmr $\delta$ 7.2–6.8 (7H,m), 4.4 (2H,s), 4.05 (2H,d), 3.95 (2H,d), 3.8 (3H, s), 3.7 (2H,s), 1.4 (6H,s).

(v) To a stirred solution of 2,2-dimethyl-5-(3,4-difluorophenyl)-5-(4-methoxybenzyloxymethyl)-1,3-dioxane (360 mg, 1 mmol) in 10 ml of an 18:1 v/v mixture of dichloromethane-water was added 2,3-dichloro-5,6-dicyano-1,4-benzoquinone (350 mg, 1.5 mmol) in small portions. The reaction mixture was stirred for 4 hours, then filtered and evaporated; purification on a silica column eluting with dichloromethane/methanol (19:1 v/v) afforded 2,2-dimethyl-5-(3,4-difluorophenyl) 5-hydroxymethyl-1,3-dioxane as a yellow oil. Nmr $\delta$ 7.2–7.0 (3H,m), 4.05 (2H,d), 4.00 (2H,d), 4.00 (2H,s), 1.75 (1H,broad), 1.4 (6H,d).

(vi) 2,2-Dimethyl-5-(3,4-difluorophenyl)-5-hydroxymethyl-1,3-dioxane (1.0 g) and Dowex 50×8-200 ion exchange resin (H+ form) (100 mg) in methanol (100 ml) containing water (20 ml) was heated to reflux with stirring for 3 hours. The cooled solution was filtered and evaporated to leave 2-(3,4-difluorophenyl)-2-hydroxymethylpropane-1,3-diol (0.45 g) as a yellow gum. Nmr. (d$_6$ acetone) $\delta$ 7.5 (1H,m), 7.3 (1H,m), 7.2 (1H,m), 3.95 (6H,s), 4.2–3.8 (3H,broad).

(vii) A mixture of trimethyl-4-bromoorthobenzoate (1.3 g, 5 mmol) (ref. European Patent Application No. 86305820.2), trimethylsilylacetylene (1 g, 10 mmol), palladium (II) acetate (150 mg) and triphenylphosphine (300 mg) in anhydrous triethylamine was heated to reflux with stirring under a nitrogen atmosphere for 1 hour. The cooled solution was evaporated to dryness, the residue partitioned between water and diethyl ether, and the organic layer was separated, dried over anhydrous magnesium sulphate and evaporated. The residue was purified on a basic alumina column, and elution with hexane afforded the trimethyl-4-trimethylsilylethynylorthobenzoate as a yellow liquid (1.2 g, 87%), Nmr δ 7.5 (4H, d of d), 3.1 (9H,s), 0.25 (9H,s).

(viii) Using the procedure described in stage (ii) of Example 4, trimethyl-4-ethynylorthobenzoate was prepared as a yellow solid, mp 62°–64° C., [M+1]+ 207, Nmr δ 7.5 (4H,d) of d), 3.1 (9H,s), 3.1 (1H,s) from trimethyl-4-trimethylsilylethynylorthobenzoate.

(ix) A mixture of 2-(3,4-difluorophenyl)-2-hydroxymethylpropane-1,3-diol (0.45 g, 2.1 mmol), trimethyl 4-ethynylorthobenzoate (0.4 g, 1.9 mmol) and p-toluene-sulphonic acid (10 mg) was heated at 140° C. under reduced pressure (30 mm Hg) for 20 minutes. The cooled residue was purified on a basic alumina column and elution with hexane/dichloromethane (4:1 v/v) gave 4-(3,4-difluorophenyl)-1-(4-ethynylphenyl)-2,6,7-trioxabicyclo[2.2.2]octane (250 mg, 38%) as a yellow solid (mp 204°–205° C.).

EXAMPLE 7

1-[4-(z)-(4'-Chlorobuten-1-ynyl)phenyl]-4-cyclobutyl-2,6,7-trioxabicyclo[2.2.2]octane A mixture of 4-cyclobutyl-1-(4-ethynylphenyl)-2,6,7-trioxabicyclo[2.2.2]octane (500 mg, 1.85 mmol), cis-1,2-dichloroethylene (0.5 ml), cuprous iodide (50 mg), tetrakis(triphenylphosphine)palladium (O) (100 mg) and n.butylamine (2 ml) in dry benzene (30 ml) under a nitrogen atmosphere was stirred at room temperature for 24 hours. The resulting solution was evaporated to dryness, the residue was taken up in dichloromethane, washed with water and then dried over anhydrous potassium carbonate. The solvents were evaporated and the residue was purified on a basic alumina column, elution with hexane-dichloro methane (9:1 v/v) gave 1-[4-(z)-(4'-chlorobuten-1'-ynyl)phenyl]-4-cyclobutyl-2,6,7-trioxabicyclo[2.2.2]octane (440 mg, 72%) as white crystals mp 80°–83° C.

EXAMPLE 8

1-(4-Butadiynylphenyl)-4-cyclobutyl-2,6,7-trioxabicyclo[2.2.2]octane

To a stirred solution of 1-[4-(z)-(4'-chlorobuten-1'-ynyl)phenyl]-4-cyclobutyl-2,6,7-trioxabicyclo[2.2.2]octane (250 mg, 0.76 mmol) in dry tetrahydrofuran (25 ml) under a nitrogen atmosphere was added tetra n.butyl ammonium fluoride (2.5 ml of 1M solution in tetrahydrofuran). The mixture was stirred overnight, evaporated and the residue partitioned between water and dichloromethane. The organic layer was separated, dried and evaporated to leave a residue that was purified on basic alumina. Elution with hexane-dichloromethane (9:1 v/v) gave 1-(4-butadiynylphenyl)-4-cyclobutyl-2,6,7-trioxabicyclo[2.2.2]octane (180 mg, 81%) as tan coloured crystals mp 123°–125° C. dec.

EXAMPLE 9

4-Cyclobutyl-1-(4-ethynylphenyl)-2,6-dioxa-7-thiabicyclo[2.2.2]octane (i) 2-Cyclobutyl-2-thiomethylpropane-1,3-diol was prepared by a method analogous to that described in Example 1 stages (i) to (iv) but substituting benzylchloromethyl thioether (J. L. Wood and V. du Vigneaud, J. Biol. Chem. 1939,267) for benzylchloromethyl ether.

(ii) A mixture of 2-cyclobutyl-2-thiomethylpropane-1,3-diol (352 mg, 2 mmol), trimethyl-4-ethynylorthobenzoate (412 mg, 2 mmol) and p.toluenesulphonic acid (10 mg) was heated at 100° C. under reduced pressure (30 mmHg) for 10 minutes. The cooled residue was purified on a basic alumina column eluting with hexane-dichloromethane (9:1 v/v) to give 4-cyclobutyl-1-(4-ethynylphenyl)-2,6-dioxa-7-thiabicyclo[2.2.2]octane (330 mg, 58%) as a pale yellow solid.

EXAMPLE 10

4-Cyclobutyl-1-(4-ethynylphenyl)-2-oxa-6,7-dithiabicyclo[2.2.2]octane (i) To a stirred solution of 2-benzloxymethyl-2-cyclobutylpropane-1,3-diol (41.86 g, 167 mmol) and pyridine (30 ml, 370 mmol) in dry diethyl ether (300 ml) at 0° C. under nitrogen atmosphere was added methanesulphonyl chloride (27 ml, 350 mmol). The solution was stirred overnight, poured into ice/water and extracted with diethyl ether. The ether extracts were dried over anhydrous magnesium sulphate and evaporated to leave a residue which was purified on a silica column; elution with hexane-ether (1:1 v/v) afforded 2-benzyloxymethyl-2-cyclobutylpropan-2,3-diol dimethanesulphonate (43.7 g, 63%) as a colourless oil.

(ii) Sodium hydride (7.5 g of 80% oil dispersion, 0.25mol) was added to a stirred solution of benzylmercaptan (31 g, 0.25 mol) in dry dimethylformamide (200 ml) at 0° C. under a nitrogen atmosphere. The mixture was stirred for 30 minutes and 2-benzyloxymethyl-2-cyclobutylpropan-1,3-diol dimethanesulphonate (43.7 g, 0.11 mol) was added and the mixture was heated at 130° C. overnight. The cooled solution was poured into ice/water and extracted with diethyl ether the ether extracts were combined, dried over anhydrous magnesium sulphate and evaporated to leave 2-benzyloxymethyl-2-cyclobutylpropane-1,3-dibenzylthioether as a crude yellow oil (53.4 g).

(iii) Using the procedure to prepare 2-cyclobutyl-2-hydroxymethylpropane-1,3-diol described earlier, 2-cyclobutyl-2-hydroxymethyl propan-1,3-dithiol (11 g, 52%) was prepared as a pale yellow oil from 2-benzyloxymethyl-2-cyclobutylpropane-1,3-dibenzylthioether (0.11 mol) and sodium (1 mol).

(iv) A mixture of 2-cyclobutyl-2-hydroxymethylpropane-1,3-dithiol (600 mg, 3.1 mmol), trimethyl-4-ethynylorthobenzoate (640 mg, 3.1 mmol) and p.toluene sulphonic acid (10 mg) was heated at 120 ° C. under reduced pressure (30 mmHg) for 5 minutes. The cooled residue was purified on a basic alumina column eluting with hexane then hexane-dichloromethane (9:1 v/v) to give a 4-cyclobutyl-1-(4-ethynylphenyl)-2-oxa-6,7-dithiabicyclo[2.2.2]octane (200 mg, 21%) as a pale yellow solid.

EXAMPLE 11

4-Cyclobutyl-1-(hex-5-ynyl)-2,6,7-trithiabicyclo[2.2.2]octane (i) To a stirred solution of 2-cyclobutyl-2-hydroxymethylpropane-1,3-diol (10 g, 62.5 mmol) and pyridine (21 ml, 0.25 mol) in dry chloroform (200 ml) at 0° C. under nitrogen atmosphere was added methanesulphonyl chloride (25 g, 18 ml, 0.22 mmol). The solution was stirred overnight, poured into ice/water and extracted with chloroform. The extracts were dried over anhydrous magnesium sulphate. Evaporation afforded 2-cyclobutyl-2-hydroxymethyl-propane-1,3-diol trimethanesulphonate which was not purified further. Nmr δ 4.20[6H, s], 3.05[9H,s], 2.60[1H, m], 2.10-1.70 [6H,m].

(ii) Sodium hydride (7.2 g of 80% oil dispersion=240 mmol) was added to a stirred solution of benzylmercaptan (30 g, 240 mmol) in dry dimethylformamide (300 ml) at 0° C. under nitrogen atmosphere. The mixture was stirred for 30 minutes and then crude 2-cyclobutyl-2-hydroxymethylpropane-1,3-diol trimethanesulphonate (27.7 g 62.5 mmol) was added. The mixture was heated at 130° C. overnight, the cooled solution was poured into ice/water and extracted with diethyl ether. The ether extracts were combined, dried over anhydrous magnesium sulphate and evaporated to leave 2-benzylthio-methyl-2-cyclobutylpropane-1,3-dibenxylthioether as a crude yellow oil (40 g) Nmr δ 7.35-7.15 [15H,m], 3.65[6H,s], 2.55[6H,s], 2.50[1H,m], 1.85-1.50[6H,m].

(iii) To liquid ammonia (1 l) was added a solution of crude 2-benzylthiomethyl-2-cyclobutylpropane-1,3-dibenzylthioether (40 g, 62.5 mmol) in dry diethyl ether (100 ml). The mixture was stirred and sodium (16 g, 0.7 mmol) was added slowly. After the addition, stirring was continued for 3 hours, then ammonium chloride (37.5 g, 0.7 mol) was added carefully. The ammonia was allowed to evaporate and the residue was washed thoroughly with diethyl ether. The ether washings were combined and evaporated to leave a residue which was purified on silica eluting with hexane, to give 2-cyclobutyl-2-mercaptomethylpropane-1,3-dithiol as an oil (10.2 g, 78%) Nmr δ 2.65[6H,d], 2.05-1.60[7H,m], 1.25[3H,t].

(iv) A mixture of 2-cyclobutyl-2-mercaptomethylpropane-1,3-dithiol (4 g, 20 mmol), trimethylorthoformate (2.5 g, 24 mmol) and Amberlyst 15 ion-exchange resin (1 g) was heated to reflux with stirring under a nitrogen atmosphere for 1 hour in dry benzene (100 ml). The mixture was filtered and evaporated to leave a residue which was washed with diethyl ether to give 4-cyclobutyl-2,6,7-trithiabicyclo[2.2.2]octane as a white solid (1.8 g, 43%) mp 112°-114° C., [M+1]+ 219.

(v) To a solution of 4-cyclobutyl-2,6,7-trithiabicyclo[2.2.2]octane (2 g, 9.2 mmol) in dry tetrahydrafuran (50 ml) at −70 ° C. under a nitrogen atmosphere was added n.butyl lithium (4 ml, 0.12 mmol, 2.3M solution in hexane). After stirring for 1 hour 1-trimethylsilyl-6-iodohex-1-yne(2.6 g, 9.3 mmol) (ref.European Patent Application No. 88306718.3) was added. Stirring was continued for one hour and the mixture was allowed to warm to room temperature. After pouring into ice/water the mixture was extracted with diethyl ether, the organic layer was separated, dried over anhydrous magnesium sulphate and evaporated to give 4-cyclobutyl-1-(6-trimethylsilyhex-5-ynyl)-2,6,7-trithiabicyclo[2.2.2]octane as a white solid which was recrystallised from hexane-dichloromethane (3.2 g, 94%).

(vi) To a stirred solution of 4-cyclobutyl-1-(6-trimethysilyhex-5-ynyl)-2,6,7-trithiabicyclo[ 2.2.2]octane (1.1 g, 3 mmol) in dry tetrahydrofuran, (40 ml) was added tetra n-butylammonium fluoride (3.2 ml of 1M solution in tetrahydrofuran). The mixture was stirred under a nitrogen atmosphere for 1 hour, evaporated and the residue partitioned between water and dichloromethane. The organic layer was separated, dried over anhydrous potassium carbonate and evaporated to leave a solid which was purified by chromatography on silica. 4-Cyclobutyl-1-(hex-5-ynyl)-2,6,7-trithiabicyclo[2.2.2]octane was obtained as a colourless solid.

BIOLOGICAL ACTIVITIES

The following examples illustrate in a non-limiting manner, the pesticidal activity of compounds of formula (I)

SPRAY TESTS

The compounds of the invention were tested by dissolving the compounds in acetone (5%) and then diluting in water: 'Symperonic' (94.5%:0.5%) to give a water emulsion. The solution was then used to treat the following insects.

Musca domestica 20 female Musca were contained in a cardboard cylinder with gauze over either end. Solution containing the compound was sprayed onto the insects so enclosed and mortality assessed after 48 hours at 25° C.

The following compounds were active at <1000 ppm: 1, 5, 14, 29, 30.

The following compounds were active at <200 ppm: 2, 3, 4, 9, 10, 11, 12, 13, 15, 16, 17, 18, 19, 20, 21, 25, 27, 28, 33, 34.

Sitophilus granarius and Tribolium castaneum 20 adult Sitophilus and Tribolium were added to 10 g wheat which had been previously treated with 2 ml of the solution containing the compound. Mortality was assessed after 6 days at 25° C.

Sitophilus

The following compounds were active at <1000 ppm: 2, 5, 13, 18, 19, 27, 29, 30.

The following compounds were active at <200 ppm: 3, 4, 9 , 11, 12, 16, 17, 20, 21, 22, 24, 28, 34.

Tribolium

The following compounds were active at <1000 ppm: 1, 3, 5, 12, 17, 29, 30.

The following compounds were active at <200 ppm: 16, 20, 21, 28.

Plutella xylostella

7 Plutella larvae were sprayed with the solution containing the compound and added to a chinese cabbage leaf which had been similarly sprayed and left to dry. Alternatively 7 Plutella larvae were put onto leaf discs and sprayed with the solution containing the compound. Mortality was assessed after 2 days at 25° C.

The following compounds were active at <1000 ppm: 5, 9, 17, 29, 34.

The following compounds were active at <200 ppm: 3, 4, 16, 20, 21, 28, 30, 33.

Myzus persicae 10 adult Myzus were placed on a leaf disc of chinese cabbage. 24 Hours later the disc was sprayed with the solution containing the compound. Mortality was assessed after 2 days at 20° C.

The following compounds were active at <1000 ppm: 3, 5, 20, 33.

The following compounds were active at ≧200 ppm: 4, 9.

Tetranychus urticae

Leaf discs of infested french bean were sprayed with the solution containing the compound. Mortality was assessed after 2 days at 25° C.

The following compounds were active at <1000 ppm: 10, 12, 13, 20.

The following compounds were active <200 ppm: 5.

Spodoptera littoralis

A chinese cabbage leaf was sprayed with the solution of the compound and left to dry. It was infested with 10 newly hatched Spodoptera larvae. Mortality was assessed after 3 days at 25° C.

The following compounds were active at less than 2000 p.p.m.: 33.

Diabrotica Undecimpunctata

Filter paper and food were sprayed and subsequently infested with 10 second instar larvae. Mortality was assessed after 48 hours.

The following compounds were active at least than 200 p.p.m.:-33.

Topical Application

The activity of compounds of the invention against anaesthetised male *Blatella germanica* was demonstrated by the topical application to the test insect of a solution of the compound under test in butanone. Mortality was assessed after 6 days.

The following compounds were active at <5 μg per insect 9, 16, 18, 20, 21, 28, 30, 33.

Anaesthetised adult male *Peripleneta americana* were topically applied with a solution of the compound under test in butanone. Mortality was assessed after 6 days. The following compounds were active at less than 5 μg/insect: 33.

The activity of compounds of the invention against unanaesthetised female *Musca domestica* (WRL strain), was demonstrated by the topical application to the test insect of a solution of the compound under test in butanone. Mortality was assessed at 48 hours.

The following compounds were active at <7 μg per insect: 2, 3, 4, 8, 9, 12, 13, 15, 16, 17, 19, 20, 21, 25, 27, 28, 30, 33, 34.

TABLE 1
2,6,7-Trioxabicyclo(2.2.2) octanes

| Compound Number | R | $R^1$ | $R^3$ | Synthetic Method |
|---|---|---|---|---|
| 1. | Cyclobutyl | H | 4-Iodophenyl | 1 |
| 2. | Cyclobutyl | H | 4-Trimethylsilyl-ethynylphenyl | 4 |
| 3. | Cyclobutyl | H | 4-(Propy-1-ynyl)phenyl | 3 |
| 4. | Cyclobutyl | H | 4-Ethynylphenyl | 4 |
| 5. | Cyclobutyl | H | Hex-5-ynyl | 1 |
| 6. | Cyclobutyl | CN | 4-Iodophenyl | 2 |
| 7. | Cyclobutyl | CN | 4-Trimethylsilyl-ethynylphenyl | 4 |
| 8. | Cyclobutyl | CN | 4-Ethynylphenyl | 4 |
| 9. | Cyclobutyl | CN | Hex-5-ynyl | 2 |
| 10. | Cyclopropyl | H | 4-Iodophenyl | 1 |
| 11. | Cyclopropyl | H | 4-Trimethylsilyl-ethynylphenyl | 4 |
| 12. | Cyclopropyl | H | 4-Ethynylphenyl | 4 |
| 13. | Cyclopropyl | H | 4-(Prop-1-ynyl)phenyl | 3 |
| 14. | trans-2-Methyl-cyclopropyl | H | 4-Iodophenyl | 1 |
| 15. | trans-2-Methyl-cyclopropyl | H | 4-Trimethylsilyl-ethynylphenyl | 4 |
| 16. | trans-2-Methyl-cyclopropyl | H | 4-Ethynylphenyl | 4 |
| 17. | trans-2-Methyl-cyclopropyl | H | 4-(Prop-1-ynyl)-phenyl | 3 |
| 18. | 1-Methylcyclopropyl | H | 4-Iodophenyl | 1 |
| 19. | 1-Methylcyclopropyl | H | 4-Trimethylsilyl-ethynylphenyl | 4 |
| 20. | 1-Methylcyclopropyl | H | 4-Ethynylphenyl | 4 |
| 21. | 1-Methylcyclopropyl | H | 4-(Prop-1-ynyl)-phenyl | 3 |
| 22. | 3-Fluorophenyl | H | 4-Iodophenyl | 1 |
| 23. | 2-Fluorophenyl | H | 4-Iodophenyl | 1 |
| 24. | 4-Fluorophenyl | H | 4-Iodophenyl | 1 |
| 25. | 3-Fluorophenyl | H | 4-Trimethylsilyl-ethynylphenyl | 4 |
| 26. | 2-Fluorophenyl | H | 4-Trimethylsilyl-ethynylphenyl | 4 |
| 27. | 4-Fluorophenyl | H | 4-Trimethylsilyl-ethynylphenyl | 4 |
| 28. | 3-Fluorophenyl | H | 3-Ethynylphenyl | 4 |
| 29. | 2-Fluorophenyl | H | 4-Ethynylphenyl | 4 |
| 30. | 4-Fluorophenyl | H | 4-Ethynylphenyl | 4 |
| 31. | 4-Fluorophenyl | H | 4-Chlorophenyl | 5 |
| 32. | 2-Fluorophenyl | H | 4-Chlorophenyl | 5 |
| 33. | 3,4-Difluorophenyl | H | 4-Ethynylphenyl | 6 |
| 34. | 4-Fluorophenyl | H | 4-(Prop-1-ynyl)phenyl | 3 |
| 35. | Cyclobutyl | H | z-4-(4-Chlorobuten-1-ynyl)phenyl | 7 |
| 36. | Cyclobutyl | H | 4-Butadiynylphenyl | 8 |

TABLE 2
Characterising Data for 2,6,7-Trioxabicyclo[2.2.2]octanes

| Compound Number | Melting Point | Mass Spectrum Chemical Ionisation M + 1 | Nuclear Magnetic Resonance Spectrum $^1H$, in $CDCl_3$, p.p.m. from TMS, number protons, multiplicity. |
|---|---|---|---|
| 1. | 162-3° | 373 | 7.7, 2H, d; 7.3, 2H, d; 4.1, 6H, s; 2.25, 1H, m; 1.9-1.7, 6H, m. |
| 2. | 174-6° | 343 | 7.55, 2H, d; 7.4, 2H, d; 4.1, 6H, s; 2.25, 1H, m; 1.9-1.7, 6H, m; 0.2, 9H, s. |
| 3. | 202-203° | 285 | 7.5, 2H, d; 7.35, 2H, d; 4.1, 6H, s; 2.25, 1H, m; 2.0, 3H, s; 1.9-1.7, 6H, m. |
| 4. | 162-163° | 271 | 7.55, 2H, d; 7.45, 2H, d; 4.1, 6H, s; 3.05, 1H, s; 2.25, 1H, m; 1.9-1.7, 6H, m. |
| 5. | 26-27° | 251 | 3.85, 6H, s; 2.15, 3H, m; 1.9, 1H, t; 1.85-1.5, 12H, m. |
| 6. | 120-121° | 398 | 7.7, 2H, d; 7.3, 2H, d; 4.8, 1H, d; 4.4, 1H, dd; 4.25, 1H, d; 4.15, 1H, dd; 4.05, 1H, dd; 2.5, 1H, m; 2.0-1.7, 6H, m. |

TABLE 2-continued

Characterising Data for 2,6,7-Trioxabicyclo[2.2.2]octanes

| Compound Number | Melting Point | Mass Spectrum Chemical Ionisation M + 1 | Nuclear Magnetic Resonance Spectrum $^1$H, in CDCl$_3$, p.p.m. from TMS, number protons, multiplicity. |
|---|---|---|---|
| 7. | Solid | | 7.5, 2H, d; 7.4, 2H, d; 4.8, 1H, d; 4.4, 1H, dd; 4.25, 1H, d; 4.15, 1H, dd; 4.05, 1H, dd; 2.5, 1H, m; 2.0–1.7, 6H, m; 0.25, 9H, s. |
| 8. | 98–99° | 296 | 7.55, 2H, d; 7.45, 2H, d; 4.80, 1H, d; 4.4, 1H, dd; 4.25, 1H, d; 4.15, 1H, dd; 4.05, 1H, dd; 3.1, 1H, s; 2.5, 1H, m; 2.0–1.7, 6H, m. |
| 9. | 50–51° | 276 | 4.65, 1H, d; 4.25, 1H, dd; 4.05, 1H, d; 3.95, 1H, dd; 3.85, 1H, dd; 2.4, 1H, m; 2.15, 2H, m; 2.0–1.5, 13H, m. |
| 10. | 175–177 | 359 | 7.65, 2H, d; 7.3, 2H, d; 4.0, 6H, s; 0.55, 1H, m; 0.45, 2H, m; 0.25, 2H, m. |
| 11. | 189–191 | 329 | 7.55, 2H, d; 7.4, 2H, d; 4.0, 6H, s; 0.55, 1H, m; 0.45, 2H, m; 0.25, 2H, m; 0.2, 9H, s. |
| 12. | 180–182 | 257 | 7.55, 2H, d; 7.45, 2H, d; 4.0, 6H, s; 3.05, 1H, s; 0.55, 1H, m; 0.45, 2H, m; 0.25, 2H, m. |
| 13. | 185–187° | 271 | 7.5, 2H, d; 7.35, 2H, d; 4.0, 6H, s; 2.0, 3H, s; 0.55, 1H, m; 0.45, 2H, m; 0.25, 2H, m. |
| 14. | 129–131° | 373 | 7.65, 2H, d; 7.3, 2H, d; 4.0, 6H, s; 1.0, 3H, d; 0.65, 1H, m; 0.4, 1H, m; 0.2, 2H, m. |
| 15. | 139–141° | 343 | 7.5, 2H, d; 7.4, 2H, d; 4.0, 6H, s; 1.0, 3H, d; 0.65, 1H, m; 0.4, 1H, m; 0.2, 2H, m; 0.2, 9H, s. |
| 16. | 128–131° | 271 | 7.55, 2H, d; 7.45, 2H, d; 4.0, 6H, s; 3.05, 1H, s; 1.0, 3H, d; 0.65, 1H, m; 0.45, 1H, m; 0.2, 2H, m. |
| 17. | 194–196° | 285 | 7.5, 2H, d; 7.35, 2H, d; 4.0, 6H, s; 2.0, 3H, s; 1.0, 3H, d; 0.65, 1H, m; 0.4, 1H, m; 0.2, 2H, m. |
| 18. | 185–187° | 373 | 7.65, 2H, d; 7.3, 2H, d; 4.05, 6H, s; 1.0, 3H, s; 0.5, 2H, m; 0.2, 2H, m. |
| 19. | 235–237° | 343 | 7.5, 2H, d; 7.4, 2H, d; 4.05, 6H, s; 1.0, 3H, s; 0.5, 2H, m; 0.2, 2H, m; 0.2, 9H, s. |
| 20. | 139–142° | 271 | 7.55, 2H, d; 7.45, 2H, d; 4.05, 6H, s; 3.05, 1H, s; 1.0, 3H, s; 0.5, 2H, m; 0.2, 2H, m. |
| 21. | 195–198 | 285 | 7.5, 2H, d; 7.35, 2H, d; 4.05, 6H, s; 2.0, 3H, s; 1.0, 3H, s; 0.5, 2H, m; 0.2, 2H, m. |
| 22. | 186–7° | 413 | 7.7, 2H, d; 7.4, 2H, d; 7.35, 1H, m; 7.1–6.85, 3H, m; 4.45, 6H, s. |
| 23. | 158–161° | 413 | 7.7, 2H, d; 7.4, 2H, d; 7.35–7.0, 4H, m; 4.55, 6H, s. |
| 24. | 269–271° | 413 | 7.7, 2H, d; 7.4, 2H, d; 7.2–7.05, 4H, m; 4.45, 6H, s. |
| 25. | | 383 | 7.6, 2H, d; 7.45, 2H, d; 7.35, 1H, m; 7.1–6.85, 3H, m; 4.45, 6H, s; 0.2, 9H, s. |
| 26. | 208–9° | 383 | 7.6, 2H, d; 7.45, 2H, d; 7.35–7.0, 4H, m; 4.55, 6H, s; 0.25, 9H, s. |
| 27. | 266–268° | 383 | 7.6, 2H, d; 7.45, 2H, d; 7.2–7.05, 4H, m; 4.45, 6H, s; 0.25, 9H, s. |
| 28. | 193–194° | 311 | 7.6, 2H, d; 7.5, 2H, d; 7.35, 1H, m; 7.1–6.85, 3H, m; 4.45, 6H, s; 3.1, 1H, s. |
| 29. | 163–165° | 311 | 7.6, 2H, d; 7.5, 2H, d; 7.3, 1H, m; 7.2–7.0, 3H, m; 4.55, 6H, s; 3.1, 1H, s. |
| 30. | 239–241° | 311 | 7.6, 2H, d; 7.5, 2H, d; 7.2–7.05, 4H, m; 7.45, 6H, s; 3.1, 1H, s. |
| 31. | 251–252° | 321 | 7.6, 2H, d; 7.3, 2H, d; 7.2–7.05, 4H, m; 4.4, 6H, s. |
| 32. | 185–187° | 321 | 7.6, 2H, d; 7.3, 2H, d; 7.3, 1H, m; 7.2–7.0, 3H, m; 4.55, 6H, s. |
| 33. | 204–205° | 329 | 7.6, 2H, d; 7.5, 2H, d; 7.2, 1H, m; 7.0, 1H, m; 6.9, 1H, m; 4.40, 6H, s; 3.1, 1H, s. |
| 34. | 276–278° | 325 | 7.55, 2H, d; 7.40, 2H, d; 7.20–7.05, 4H, m; 4.45, 6H, s; 2.05, 3H, s. |
| 35. | 80–83° | 331 | 7.5, 2H, d; 7.45, 2H, d; 6.4, 1H, d; 6.05, 1H, d; 4.1, 6H, s; 2.25, 1H, m; 1.95–1.7, 6H, m. |
| 36. | 123–125° (decomposes) | 295 | 7.55, 2H, d; 7.5, 2H, d; 4.1, 6H, s; 2.5, 1H, s; 2.2, 1H, m; 1.95–1.70, 6H, m. |

TABLE 3

Thiabicyclo-octanes

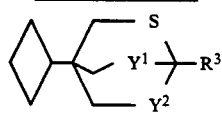

| Compound Number | R$^3$ | Y$^1$ | Y$^2$ | Synthetic method |
|---|---|---|---|---|
| 37. | 4-Ethynylphenyl | O | O | 9 |
| 38. | 4-Ethynylphenyl | S | O | 10 |
| 39. | 6-Trimethylsilyl- | S | S | 11 |

TABLE 3-continued

Thiabicyclo-octanes

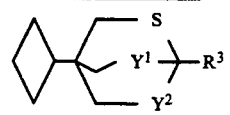

| Compound Number | R$^3$ | Y$^1$ | Y$^2$ | Synthetic method |
|---|---|---|---|---|
| 40. | hex-5-ynyl Hex-5-ynyl | S | S | 11 |

TABLE 4

Characterising Data for Thiabicyclo-octanes

| Compound Number | Melting Point | Mass Spectrum Chemical Ionisation M + 1 | Nuclear Magnetic Resonance Spectrum $^1$H, in CDCl$_3$, p.p.m. from TMS, number of protons, multiplicity. |
| --- | --- | --- | --- |
| 37. | 163–5° | 287 | 7.55, 2H, d; 7.45, 2H, d; 4.15, 4H, dd; 3.05, 1H, s; 3.0, 2H, s; 2.25, 1H, m; 1.9–1.7, 6H, m. |
| 38. | 141–143° | 303 | 7.6, 2H, d; 7.45, 2H, d; 4.15, 2H, s; 3.1, 4H, s; 3.05, 1H, s; 2.3, 1H, m; 1.95–1.7, 6H, m. |
| 39. | 130–132° | 371 | 2.95, 6H, s; 2.35, 1H, m; 2.25, 2H, t; 2.00, 2H, m; 1.95–1.55, 10H, m; 0.13, 9H, s. |
| 40. | 70–71° | 299 | 2.95, 6H, s; 2.35, 1H, m; 2.20, 2H, dt; 2.00, 2H, m; 1.93, 1H, t; 1.90–1.50, 10H, m. |

We claim:

1. A compound of the formula:

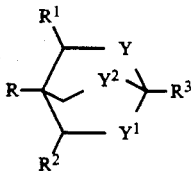

(I)

wherein

R is a phenyl group substituted by fluorine in the meta, para, both meta and para or ortho, meta and para positions;

R$^1$ and R$^2$ may be the same or different, and each is hydrogen, halo, or a C$_{1-3}$ aliphatic group optionally substituted by halo, cyano, C$_{2-5}$ carbalkoxy, C$_{1-4}$ alkoxy, or a group S(O)$_m$R$^{11}$ wherein m is 0, 1 or 2 and R$^{11}$ is C$_{1-4}$ alkyl, cyano, gem dimethyl, or C$_{2-5}$ carbalkoxy;

R$^3$ contains between 3 and 18 carbon atoms and is a group R$^{12}$ wherein R$^{12}$ is a C$_{1-13}$ non-aromatic hydrocarbyl group, optionally substituted by a C$_{2-4}$ carbalkoxy or cyano group and/or by one or two hydroxy groups and/or by one to five halo atoms which are the same or different and/or by one to three groups R$^{13}$ which are the same or different and each include alkyloxy, alkenyloxy, alkynyloxy, alkoxyalkoxy, acyloxy, alkynyloximino, trialkylsilyl, haloalkyloxy, haloalkenyloxy, haloalkylnyloxy, alklyoximino, alkoxycarbonyloxy and mono or di-substituted alkylamino groups, or a group —(O)$_n$S(O)$_r$(O)$_w$R$^{19}$ wherein R$^{19}$ is a C$_{1-4}$ aliphatic group optionally substituted by halo, n is 0 or 1, r is 0, 1 or 2 and w is 0 or 1, the sum of n, r and w is between 0 and 3, or $_q$R$^3$ is phenyl or phenyl substituted by cyano and/or by one to five halo atoms and/or by one to three C$_{1-4}$ haloalkyl groups and/or by a group —C≡CH, C≡C-halo or —C≡C—R$^{12}$ wherein R$^{12}$ is as hereinbefore defined or —C≡C—R$^{14}$ wherein R$^{14}$ is a group S(O)$_q$R$^{15}$ wherein R$^{15}$ is methyl, ethyl or trifluoromethyl and q is 0, 1 or 2, or R$^{14}$ is SiR$^{16}$R$^{17}$R$^{18}$ wherein R$^{16}$ and R$^{17}$ are the same or different and are each C$_{1-4}$ aliphatic groups and R$^{18}$ is a C$_{1-4}$ aliphatic group or phenyl provided that R$^{16}$ and R$^{17}$ and R$^{18}$ do not contain more than 10 carbon atoms in total; and Y, Y$^1$ and Y$^2$ are oxygen.

2. A compound according to claim 1 wherein R$^1$ is hydrogen, cyano, methyl or ethyl each optionally substituted by cyano, methoxy, methylthio, chloro, bromo or fluoro.

3. A compound according to claim 1 wherein R$^2$ is hydrogen, cyano, methyl or trifluoromethyl.

4. A compound according to claim 1 wherein R$^3$ is a phenyl group substituted at the 3-,4- or 5-positions by one to three substituents each selected from halo, C$_{1-4}$ haloalkyl, cyano, or a group (C≡C)$_p$R$^{20}$ wherein p is 1 or 2 and R$^{20}$ is hydrogen, bromo, chloro or iodo; or R$^{20}$ is an aliphatic group containing up to five carbon atoms optionally substituted by C$_{1-4}$ alkoxy, C$_{1-6}$ alkoxyalkoxy, C$_{1-8}$ acyloxy, halo or hydroxy; or R$^{20}$ is SiR$^{16}$R$^{17}$R$^{18}$ wherein R$^{16}$ and R$^{17}$ and R$^{18}$ are as hereinbefore defined and the phenyl group is additionally optionally substituted at the 2- and/or 6-positions by fluoro or chloro.

5. A compound according to claim 1 wherein R$^3$ is phenyl substituted at the 3-, 4- or 5- position by one to three substituents each selected from halo, cyano, C$_{1-4}$ haloalkyl or group C≡C—R$^{21}$ where R$^{21}$ is hydrogen, methyl, or ethyl each optionally substituted by hydroxy, methoxy, ethoxy, acetoxy; or R$^{21}$ is ethynyl, or a silyl group substituted by three C$_{1-4}$ alkyl groups, R$^3$ is additionally optionally substituted at the 2- and/or 6-positions by fluoro or chloro.

6. A compound according to claim 1 wherein R$^3$ is a group —B(C≡C)Z, wherein B is a C$_{3-5}$ aliphatic chain optionally containing a double bond and/or an oxygen atom and/or a group S(O)$_q$ wherein q is 0, 1 or 2, and optionally substituted by halo, C$_{1-4}$ alkyl, C$_{1-4}$ haloalkyl, C$_{2-4}$ carbalkoxy or cyano and Z is hydrogen, C$_{1-5}$ alkyl, C$_{1-3}$ alkoxymethyl or a group SiR$^{16}$R$^{17}$R$^{18}$ wherein R$^{16}$, R$^{17}$ and R$^{18}$ are as hereinbefore defined.

7. A compound according to claim 1 wherein R$^3$ is a group -DZ$^1$, wherein D is a group —CH$_2$O— or CH$_2$S(O)$_q$ wherein q is 0, 1 or 2 or a C$_{2-3}$ aliphatic group each of which may be optionally substituted by one to three halo atoms and Z$^1$ is silyl substituted by three C$_{1-4}$ alkyl groups or Z$^1$ is a group

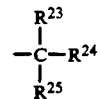

wherein R$^{23}$, R$^{24}$ and R$^{25}$ are the same or different and are each independently selected from halo, cyano, C$_{2-5}$ carbalkoxy, or a C$_{1-4}$ aliphatic group optionally substituted by halo, cyano, C$_{2-5}$ carbalkoxy, C$_{1-4}$ alkoxy or a group S(O)$_q$R$^{26}$ wherein q is 0, 1 or 2 and R$^{26}$ is C$_{1-4}$ alkyl, or R$^{23}$, R$^{24}$ and R$^{25}$ are selected from C$_{1-4}$ alkoxy or a group S(O)$_z$R$^{27}$ wherein z is 0, 1 or 2 and R$^{27}$ is C$_{1-4}$ alkyl optionally substituted by fluoro or R$^{23}$ and R$^{24}$ are linked to form a C$_{3-6}$ cycloalkyl ring, or one of R$^{23}$, R$^{24}$ and R$^{25}$ may be hydrogen.

8. A compound of the formula (I) according to claim 1 wherein $R^3$ is a group

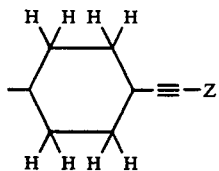

wherein Z is hydrogen, $C_{1-5}$ alkyl, $C_{1-3}$ alkoxymethyl or $SiR^{16}R^{17}R^{18}$.

9. An insecticidal or acaricidal composition comprising a compound of formula (I) as defined in claim 1 in admixture with a carrier or diluent.

10. A method for the control of pests comprising application to the pest or to an environment susceptible to pest infestation of a pesticidally effective amount of a compound according to claim 1.

11. A method for the control of pests on plants comprising application to the pest or the plant of a pesticidally effective amount of a compound according to claim 1.

12. A method for the control of pests on animals or humans comprising application to the pest, animal or human of a pesticidally effective amount of a compound according to claim 1.

* * * * *